(12) United States Patent
Abbott et al.

(10) Patent No.: US 11,998,292 B2
(45) Date of Patent: Jun. 4, 2024

(54) CONTROL OF COMPUTER-ASSISTED TELE-OPERATED SYSTEMS

(71) Applicant: Intuitive Surgical Operations, Inc., Sunnyvale, CA (US)

(72) Inventors: Ryan Charles Abbott, San Jose, CA (US); John Ryan Steger, Sunnyvale, CA (US); Daniel H. Gomez, Los Gatos, CA (US); Ian E. McDowall, Woodside, CA (US); Amy Kerdok, San Jose, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 448 days.

(21) Appl. No.: 17/474,419

(22) Filed: Sep. 14, 2021

(65) Prior Publication Data

US 2021/0401518 A1 Dec. 30, 2021

Related U.S. Application Data

(63) Continuation of application No. 16/484,280, filed as application No. PCT/US2018/015302 on Jan. 25, 2018, now Pat. No. 11,154,373.

(Continued)

(51) Int. Cl.
*A61B 34/35* (2016.01)
*A61B 17/00* (2006.01)
(Continued)

(52) U.S. Cl.
CPC .............. *A61B 34/35* (2016.02); *A61B 34/76* (2016.02); *A61B 2017/00464* (2013.01);
(Continued)

(58) Field of Classification Search
CPC .......... A61B 34/35; A61B 2017/00327; A61B 2017/00323; A61B 2017/00318;
(Continued)

(56) References Cited

U.S. PATENT DOCUMENTS 7,736,254 B2 6/2010 Schena
2010/0082041 A1 4/2010 Prisco
(Continued)

FOREIGN PATENT DOCUMENTS

| WO | WO-2011060046 A2 | 5/2011 |
|---|---|---|
| WO | WO-2015142290 A1 | 9/2015 |
| WO | WO-2016189284 A1 | 12/2016 |

OTHER PUBLICATIONS

International Search Report and Written Opinion for Application No. PCT/US2018/015302, dated Jun. 22, 2018, 11 pages.
(Continued)

*Primary Examiner* — Tan-Uyen T Ho
*Assistant Examiner* — Bridget E. Rabaglia
(74) *Attorney, Agent, or Firm* — Osha Bergman Watanabe & Burton LLP

(57) ABSTRACT

An instrument system includes an instrument, a drive system, and a controller operably connected to a first drive mechanism and a second drive mechanism of the drive system. The controller is configured to operate the first drive mechanism and the second drive mechanism drive a flexible tensioning member of the instrument to cause movement of an end effector of the instrument while maintaining a tension applied to the flexible tensioning member of the instrument in a tension range.

21 Claims, 17 Drawing Sheets

Related U.S. Application Data

(60) Provisional application No. 62/456,262, filed on Feb. 8, 2017.

(51) Int. Cl.
*A61B 34/00* (2016.01)
*A61B 90/00* (2016.01)
*A61B 90/57* (2016.01)
*G16H 40/60* (2018.01)

(52) U.S. Cl.
CPC .............. *A61B 2017/00477* (2013.01); *A61B 2034/715* (2016.02); *A61B 2090/065* (2016.02); *A61B 2090/066* (2016.02); *A61B 2090/0809* (2016.02); *A61B 2090/571* (2016.02); *G16H 40/60* (2018.01)

(58) Field of Classification Search
CPC .... A61B 2017/003; A61B 2017/00292; A61B 17/00234; A61B 2034/715; A61B 2017/00464; A61B 2017/00477; A61B 2090/065; A61B 34/76; A61B 34/30; A61B 2034/301; A61B 2034/302; A61B 2034/303; A61B 2034/304; A61B 2034/305; A61B 2034/306; A61B 34/72; A61B 34/71

See application file for complete search history.

(56) References Cited

U.S. PATENT DOCUMENTS

2011/0106141 A1* 5/2011 Nakamura ............. A61B 34/71
606/205
2016/0213438 A1* 7/2016 Jogasaki ................. A61B 1/00

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

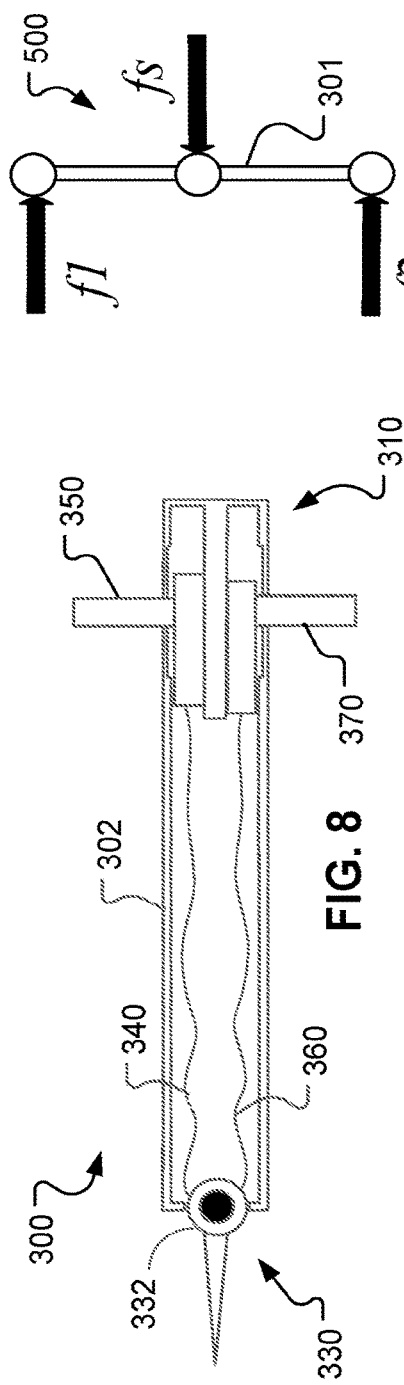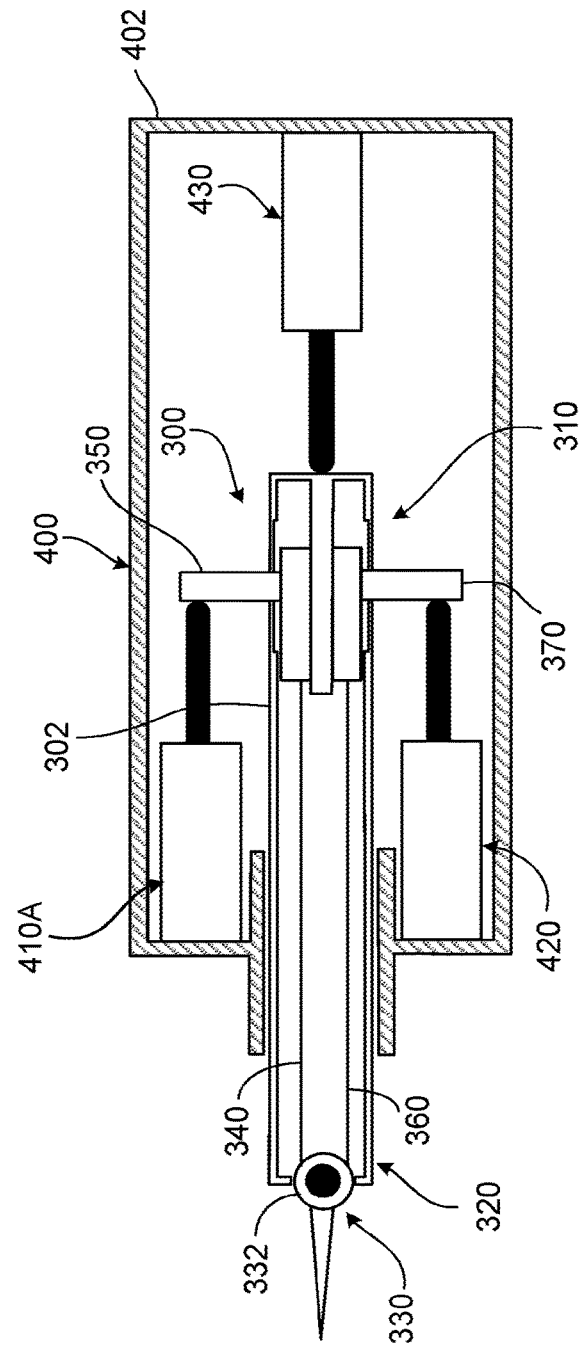

CONTROL OF COMPUTER-ASSISTED TELE-OPERATED SYSTEMS

CROSS-REFERENCES TO RELATED APPLICATIONS

This application is a continuation of U.S. patent application Ser. No. 16/484,280, filed on Aug. 7, 2019, which is a U.S. National Stage Application under 35 U.S.C § 371 and claims the benefit of International Patent Application No. PCT/US2018/015302, filed on Jan. 25, 2018, which claims the benefit of U.S. Provisional Application No. 62/456,262, filed on Feb. 8, 2017. The disclosures of the prior applications are considered part of and are incorporated herein by reference in the disclosure of this application.

TECHNICAL FIELD

This disclosure relates to control of computer-assisted tele-operated system, including medical systems such as surgical systems.

BACKGROUND

Robotic systems and computer-assisted devices often include multiple robots or movable manipulators operable to manipulator surgical instruments for performing a task at a surgical work site. The robots can include at least one robot or movable manipulator for supporting an image capturing device that captures images of the surgical work site. A robot manipulator can include interconnected links that are coupled together by one or more actively controlled joints. The manipulator can include one or more passive joints that are not actively controlled and comply with movement of an actively controlled joint.

The robotic systems can include industrial and recreational robotic systems. Robotic systems also include medical robotic systems used in procedures for diagnosis, non-surgical treatment, surgical treatment, etc. As a specific example, robotic systems include minimally invasive, computer-assisted, telesurgical systems that allow a surgeon to operate on a patient from bedside or a remote location. Telesurgery is a general term for surgical systems in which the surgeon, rather than directly holding and moving all parts of the instruments by hand, uses some form of indirect or remote control, e.g., a servomechanism, or the like, to manipulate surgical instrument movements. The surgical instruments for such surgical systems can be inserted through minimally invasive surgical apertures or natural orifices to treat tissues at sites within the patient, often reducing the trauma generally associated with accessing a surgical worksite by open surgery techniques.

These computer-assisted tele-operated systems can move end effectors of the instruments with sufficient dexterity to perform industrial, recreational, medical (including surgical) tasks. Such tasks may pivoting shafts of the instruments, sliding of the shaft axially (such as through an aperture if applicable), rotating of the shaft (such as outside of or within an aperture if an aperture is used), and/or the like.

SUMMARY

This disclosure provides devices and methods for using a computer-assisted tele-operated device. For example, this disclosure relates to instruments for computer-assisted tele-operated tasks that are controllable to maintain tensions on tensioning members of the instruments. The devices and methods provided herein can be used in conjunction with computer-assisted tele-operated systems, including medical and non-medical systems. For example, the techniques provided herein can be used with teleoperated or robotic surgery systems that use hardware-constrained remote centers of motion, software-constrained remote centers of motion, or a combination of hardware- and software-constrained remote centers of motion.

In an aspect, an instrument system comprises an instrument, a drive system, and a controller. The instrument comprises an instrument shaft, a first engagement member at a proximal portion of the instrument, a second engagement member at the proximal portion, a third engagement member coupled to the instrument shaft, an end effector, and a flexible tensioning member. The flexible tensioning member comprises a first portion and a second portion. The first portion extends between the end effector and the first engagement member, and the second portion extends between the end effector and the second engagement member. The drive system comprises a first drive mechanism, a second drive mechanism, and a third drive mechanism. The first drive mechanism is to engage with the first engagement member and drive the flexible tensioning member. The second drive mechanism is to engage with the second engagement member and drive the flexible tensioning member in opposition to the first drive mechanism. The third drive mechanism is to engage with the third engagement member and drive the instrument shaft through the third engagement member, The controller is operably connected to the first drive mechanism, the second drive mechanism, and the third drive mechanism. The controller is configured to cause a movement of the end effector while maintaining a tension applied to the flexible tensioning member within a tension range by: operating the first and second drive mechanisms to drive the flexible tensioning member, and operating the third drive mechanism to drive the instrument shaft.

In another aspect, an instrument drive system comprises a first drive actuator, a second drive actuator, a third drive actuator, and a controller. The first drive actuator is configured to engage with a first engagement member of an instrument to drive a flexible tensioning member of the instrument. The second drive actuator is configured to engage with a second engagement member of the instrument to drive the flexible tensioning member in opposition to the first drive actuator. The third drive actuator is configured to engage with a third engagement member of the instrument to drive an instrument shaft of the instrument. The controller is configured to operate the first drive actuator, the second drive actuator, and the third drive actuator to apply tension to the flexible tensioning member and cause movement of an end effector of the instrument in a first degree of freedom while maintaining the tension applied to the flexible tensioning member in a tension range.

In another aspect, a method of operating an instrument system comprising an instrument, a first drive mechanism coupled to a flexible tensioning member of the instrument, a second drive mechanism coupled to the flexible tensioning member, and a third drive mechanism coupled to a shaft of the instrument. The method comprises operating the first, second, and third drive mechanisms to apply tension to the flexible tensioning member of the instrument and cause movement of an end effector of the instrument in a first degree of freedom while maintaining the tension applied to the flexible tensioning member in a tension range.

In another aspect, a method of operating a drive system for an instrument, the method comprises receiving a commanded movement of an end effector of an instrument, determining a first tension to be applied on a first portion of a flexible tensioning member of the instrument, determining a second tension to be applied on a second portion of the flexible tensioning member, and determining a force to be applied on a shaft of the instrument. The flexible tensioning member is coupled to the end effector of the instrument. At least one of the first and second tensions is in a tension range. The method further comprises operating the drive system to apply the first tension on the first portion of the flexible tensioning member, the second tension on the second portion of the flexible tensioning member, and the force on the shaft of the instrument to cause the commanded movement of the end effector while maintaining the at least one of the first and second tensions in the tension range.

In another aspect, a non-transitory machine-readable medium comprising a plurality of machine-readable instructions. These instructions, when executed by one or more processors, are adapted to cause the one or more processors to perform any of the methods described herein.

In another aspect, an instrument system includes an instrument including a first engagement member at a proximal portion (e.g. at a proximal end portion such as a proximal end) of the instrument, a second engagement member at the proximal portion, an end effector movable in a first direction in a degree of freedom and in a second direction in a degree of freedom, and a flexible tensioning member extending between the end effector and the first engagement member and between the end effector and the second engagement member. The second direction is opposite the first direction. The instrument system further includes a drive system and a controller. The drive system includes a first drive mechanism engaged to the first engagement member to drive the flexible tensioning member a second drive mechanism engaged to the second engagement member of the instrument to drive the flexible tensioning member of the instrument in opposition to the first drive mechanism. The controller is operably connected to the first drive mechanism and the second drive mechanism. The controller is configured to operate both the first drive mechanism and the second drive mechanism to apply tension to the flexible tensioning member to cause movement of the end effector of the instrument in a degree of freedom while maintaining the tension applied to the flexible tensioning member of the instrument in a tension range.

In another aspect, an instrument drive system includes a first drive actuator positioned to engage a first engagement member of an instrument to drive a flexible tensioning member of the instrument, a second drive actuator positioned to engage a second engagement member of the instrument to drive the flexible tensioning member of the instrument in opposition to the first drive actuator, and a controller operably connected to the first drive actuator and the second drive actuator. The controller is configured to operate both the first drive actuator and the second drive actuator to apply tension to the flexible tensioning member of the instrument to cause movement of an end effector of the instrument in a first degree of freedom while maintaining the tension applied to the flexible tensioning member of the instrument in a tension range.

In another aspect, a method includes applying tension to a tensioning member of an instrument to cause movement of an end effector of the instrument in a first degree of freedom by operating first and second drive mechanisms coupled to a flexible tensioning member of the instrument, and maintaining the tension applied to the flexible tensioning member in a tension range by operating the first and second drive mechanisms while the end effector moves in the first degree of freedom.

Certain implementations can include one or more of the following features described below and herein elsewhere, including any appropriate combination of the implementations described below and herein elsewhere.

In some implementations, the instrument system is a medical instrument system (such as a diagnostic or therapeutic system that is surgical or non-surgical), and the instrument is a medical instrument.

In some implementations, the end effector is moveable in a first direction in a first degree of freedom and in a second direction in the first degree of freedom, where the second direction is opposite the first direction.

Some implementations maintain the tension applied to the flexible tensioning member by maintaining the tension at a target tension, above a minimum tension, below a maximum tension, or above a minimum tension and below a maximum tension. In some implementations, the tension range is expressed with a minimum tension, and the tension is maintained above the minimum tension. In some implementations, the tension range is expressed with a maximum tension, and the tension is maintained below the maximum tension. In some implementations, the tension range is expressed with both minimum and maximum tensions, and the tension is maintained above the minimum tension and below the maximum tension. In some implementations, the tension range is expressed with a target tension, and the tension is maintained at the target tension, or within a defined extent of the target tension.

In some implementations, operating the first and second drive mechanisms to drive the flexible tensioning member comprises operating the first drive mechanism to apply a first tension on the first portion of the flexible tensioning member, and operating the second drive mechanism to apply a second tension on the second portion of the flexible tensioning member. The first tension and the second tension may differ by a tension difference sufficient to cause the movement of the end effector.

In some implementations, the controller is configured to cause the movement of the end effector while maintaining the tension applied to the flexible tensioning member in the tension range by using a tension difference. The controller is configured to determine the tension difference to be applied on the flexible tensioning member to cause the movement of the end effector, and to determine a first tension and a second tension based on the tension difference and the tension range. The controller operates the first drive mechanism to apply the first tension on the first portion of the flexible tensioning member, and operates the second drive mechanism to apply the second tension on the second portion of the flexible tensioning member. In some implementations, determining the first tension and the second tension based on the tension difference and the tension range comprises offsetting the tension difference by a minimum tension associated with the tension range.

In some implementations, the flexible tensioning member includes a first tensioning member comprising the first portion and a second tensioning member comprising the second portion, and maintaining the tension applied to the flexible tensioning member in a tension range comprises maintaining a first tension applied to the first tensioning member in a first tension range, and maintaining a second tension applied to the second tensioning member in a second tension range.

In some implementations, the first drive mechanism comprises a first drive actuator and a first drivetrain, and the second drive mechanism comprises a second drive actuator and a second drivetrain. The first drivetrain is configured to engage with the first engagement member, and the second drivetrain is configured to engage with the second engagement member. The first drive actuator is configured to drive the first drivetrain to move the first engagement member along a longitudinal axis of the instrument, and the second drive actuator is configured to drive the second drivetrain to move the second engagement member along the longitudinal axis.

In some implementations, the movement of the end effector is parallel or perpendicular to a longitudinal axis of the instrument. In some implementations, the movement of the end effector comprises a rotational movement.

In some implementations, the instrument further comprises an instrument housing to which the first engagement member, the second engagement member, and the third engagement member are mounted. In some implementations, the flexible tensioning member extends through the instrument shaft. In some implementations, the controller is further configured to operate the third drive mechanism to cause movement of the instrument shaft.

In some implementations, the controller is configured to operate the third drive mechanism to cause movement of the instrument shaft by driving the third drive mechanism to pull or push the instrument shaft to translate the instrument shaft relative to the instrument housing. In some implementations, the movement of the end effector corresponds to any one or combination of: a pitching of the end effector, a yawing of the end effector, and a change in a grip of the end effector, and the movement of the instrument shaft corresponds to translation of the end effector. In some implementations, the translation of the instrument shaft is along an insertion axis. In some implementations, the controller is further configured to operate the third drive mechanism to lock the end effector.

In some implementations, the instrument system further comprises a sensor to detect a force in the first drive mechanism, and operating the first and second drive mechanisms to drive the flexible tensioning member comprises using the detected force. In some implementations, the instrument system further comprises a sensor to detect a force in the first drive mechanism, and operating the third drive mechanism to drive the instrument shaft comprises using the detected force. In some implementations, operating the third drive mechanism comprises determining a shaft force to be applied by the third drive mechanism based on the detected force, and operating the third drive mechanism to apply the shaft force to the instrument shaft.

In some implementations, the detected force is used in determining a friction force on the flexible tensioning member, and the friction force is in maintaining the tension applied to the flexible tensioning member in the tension range. In some implementations, the detected force is used in determining an amount of preload in the flexible tensioning member based on the detected force, and the amount of preload is used in maintaining the tension. In some implementations, the controller is further configured to issue an alarm in response to the detected force being indicative of a malfunction or breakage in the instrument or the drive system, or being indicative of a force applied by the end effector exceeding a threshold force. Example malfunctions or breakages in the instrument include a failure of the flexible tensioning member. In some implementations, the controller is further configured determine a force applied by the end effector based on the detected force.

In some implementations, the flexible tensioning member includes a first tensioning member extending between the end effector and the first engagement member and a second tensioning member extending between the end effector and the first engagement member. The controller is, for example, configured to operate both the first drive mechanism and the second drive mechanism to apply a first tension to the first tensioning member and a second tension to the second tensioning member to cause movement of the end effector of the surgical instrument in the degree of freedom while maintaining the first tension in a first tension range and while maintaining the second tension in a second tension range.

In some implementations, the first drive mechanism further includes a first drive actuator to drive a first drivetrain engaged to the first engagement member. The first drive actuator is, for example, configured to drive the first drivetrain to move the first engagement member of the surgical instrument along a longitudinal axis of the surgical instrument. The second drive mechanism further includes, for example, a second drive actuator to drive a second drivetrain engaged to the second engagement member. The second actuator is, for example, configured to drive a second drivetrain to move the second engagement member of the surgical instrument along the longitudinal axis of the surgical instrument.

In some implementations, the degree of freedom is parallel to a longitudinal axis of the surgical instrument.

In some implementations, the degree of freedom is perpendicular to a longitudinal axis of the surgical instrument.

In some implementations, the surgical instrument includes a third engagement member at the proximal portion, an instrument housing to which the first engagement member, the second engagement member, and the third engagement member are mounted, and an instrument shaft through which the flexible tensioning member extends. The drive system, for example, includes a third drive mechanism positioned to engage the third engagement member of the surgical instrument to move an instrument shaft relative to an instrument housing. The controller is, for example, configured to operate the third drive mechanism to cause movement of the end effector in another degree of freedom. In some cases, the third drive mechanism is configured to push the instrument shaft to translate the instrument shaft relative to the instrument housing and to cause movement of the end effector in the other degree of freedom. In some cases, the controller is configured to operate the first drive mechanism, the second drive mechanism, and the third drive mechanism to move the end effector in the degree of freedom while maintaining the tension in the flexible tensioning member in the tension range. In some cases, the degree of freedom corresponds to pitch, yaw, grip, or a combination thereof, and the other degree of freedom corresponds to motion along an insertion axis of the surgical instrument. In some cases, the controller is configured to operate the third drive mechanism to lock the end effector.

In some implementations, the surgical instrument system further includes a force sensor to detect a force in the first drive mechanism. The controller is, for example, configured to operate the first drive mechanism and the second drive mechanism based on the force in the first drive mechanism. In some cases, the controller is configured to determine a friction force on the flexible tensioning member based on the detected force and maintain the tension in the flexible tensioning member in the tension range based on the friction force. In some cases, the controller is configured to determine an amount of preload in the flexible tensioning member based on the detected force and maintain the tension in the flexible tensioning member in the tension range based on the amount of preload in the flexible tensioning member. In some cases, the controller is configured to issue an alarm in response to the detected force being indicative of a break in the flexible tensioning member. In some cases, the controller is configured to measure a force applied by the end effector based on the detected force.

In some implementations, the surgical instrument drive system includes a third drive actuator positioned to engage a third engagement member of the surgical instrument to move an instrument shaft relative to an instrument housing. The controller is, for example, configured to operate the third drive actuator to cause movement of the end effector in another degree of freedom.

In some implementations, applying the tension includes operating a third drive mechanism to move a shaft of the surgical instrument relative to a housing of the surgical instrument and to cause movement of the end effector in another degree of freedom. In some cases, maintaining the tension in the tension range includes maintaining the tension in the tension range by operating the first, second, and third drive mechanisms.

In some implementations, applying the tension to the flexible tensioning member includes operating both the first drive mechanism and the second drive mechanism to apply a first tension to a first tensioning member of the flexible tensioning member and a second tension to a second tensioning member of the flexible tensioning member to cause movement of the end effector of the surgical instrument in the degree of freedom while operating the first drive mechanism and the second drive mechanism to maintain the first tension in a first tension range and the second tension in a second tension range.

In some implementations, maintaining the tension in the tension range includes maintaining the tension based on a force in the first drive mechanism.

In some implementations, maintaining the tension in the tension range includes maintaining the tension based on a friction force on the flexible tensioning member.

In some implementations, maintaining the tension in the tension range includes maintaining the tension in the tension range based on an amount of preload in the flexible tensioning member.

In some implementations, the method further includes issuing an alarm in response to a break in the flexible tensioning member.

Some or all of the implementations described herein may provide one or more of the following advantages. Instruments in accordance to these implementations can be controlled in a manner to maintain tensions on the tensioning members of the instruments such that the instruments are more rapidly responsive to loads applied by the drive systems. The tensions can be considered preloads applied to the tensioning members that enable output motion of the end effector to be more precisely controlled.

As an example of another potential advantage, the instruments can further be controlled in a manner that enables errors to be easily detected. Sensors associated with the drive system used to drive tensioning members of an instrument can generate signals indicative of a condition or an error associated with the surgical instrument. In some cases, breaks of the tensioning members can be easily detected based on sensors of the drive system driving the cables. Furthermore, these same sensors can be used to maintain the pre-tensions in the cables above minimum amounts of tension.

Although the specific examples presented in this disclosure often discuss surgical examples, the techniques disclosed are also applicable to non-surgical use. For example, they may be used with and improve general or industrial robotic operations, such as those use in manipulating work pieces. These techniques may also be used with and improve medical robotic operations for diagnoses and non-surgical treatment.

Further, although the specific examples presented in this disclosure often discuss teleoperational robotic systems and remotely controllable manipulators, the techniques disclosed are also applicable to robotic systems that are directly and manually moved by operators, in part or in whole. For example, these techniques can be applied to robotic systems designed to help steady an instrument held by the robotic manipulator while the instrument is manipulated hand of an operator. As another example, any of the controllable manipulators discussed herein may be configured to allow direct manipulation, and accept operator instruction through input directly applied to a link or a joint of the manipulator.

The details of one or more implementations are set forth in the accompanying drawings and the description below. Other features, objects, and advantages will be apparent from the description and drawings, and from the claims.

BRIEF DESCRIPTION OF THE DRAWINGS

FIG. 8 is a schematic diagram of an example tele-operated instrument.

FIG. 9A is a schematic diagram of the tele-operated instrument of FIG. 8 coupled with an example instrument drive system.

FIG. 10 is a force diagram pertaining to the instrument and drive system of FIG. 9A.

Like reference symbols in the various drawings indicate like elements.

DETAILED DESCRIPTION

A computer-assisted teleoperated system includes one or more drive systems to control a position of an instrument within an environment. In some examples, a remotely controllable or otherwise teleoperated manipulator is operated to move the instrument in its entirety about the environment. In further examples, the one or more drive systems are operable to control a position of the instrument relative to the manipulator and/or to control a position of an end effector relative to a shaft of the instrument. As described herein, the one or more drive systems can be controlled in a manner to maintain tensions in tensioning members used to drive the end effector. Sensors associated with the one or more drive systems can also be used to detect conditions of the instrument, and readings from these sensors can be used to inform a user of the conditions of the instrument.

Although some of the examples described herein refer to surgical procedures or instruments, or medical procedures and medical instruments, the techniques disclosed apply to non-medical procedures and non-medical instruments. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical, medical treatment or diagnosis procedures.

Further, although some of the examples presented in this disclosure discuss teleoperational robotic systems or remotely operable systems, the techniques disclosed are also applicable to computer-assisted systems that are directly and manually moved by operators, in part or in whole. For example, these techniques can be applied to robotic systems designed to help steady a instrument held by the robotic manipulator while the instrument is manipulated by a hand of an operator. As another example, the manipulators discussed herein may be configured to allow direct manipulation, and accept operator instruction through input directly applied to a link or a joint of the manipulator.

Example Systems

Figure 1A:
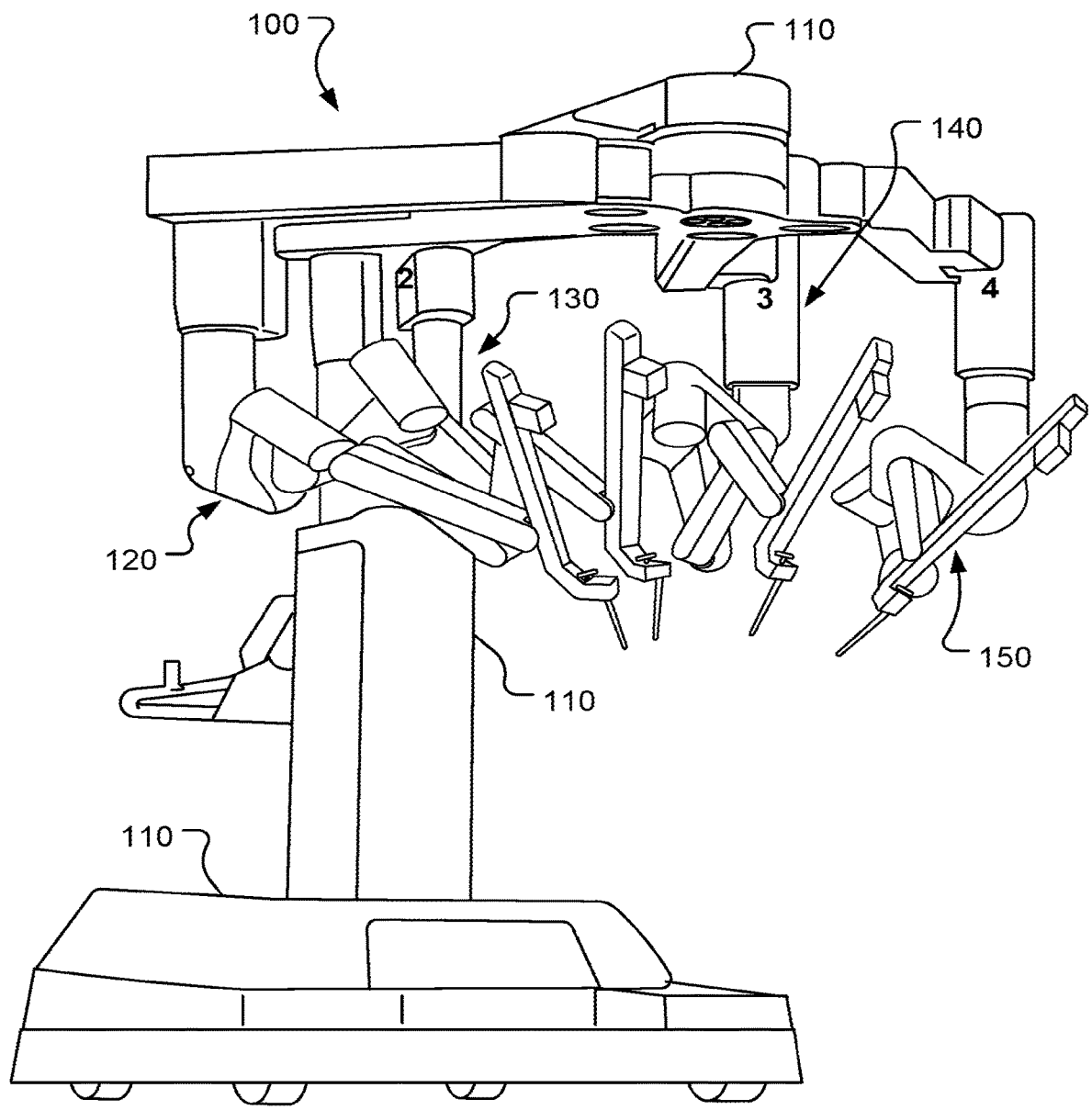
FIG. 1A is a perspective view of an example patient-side computer-assisted tele-operated system.

Example systems are described in connection with FIGS. 1 and 2. Specifically, example surgical systems for minimally invasive computer-assisted telesurgery depicted in FIGS. 1 and 2 include a patient-side cart 100 and an operator console 40 (in this particular example, the operator console comprises a surgeon console that is usually used by surgical personnel such as surgeons). The patient-side cart 100 includes a base 110, a first remotely controllable manipulator system 120, a second remotely controllable manipulator system 130, a third remotely controllable manipulator system 140, and a fourth remotely controllable manipulator system 150. Each manipulator system 120, 130, 140, and 150 is pivotably coupled to the base 110. In some implementations, fewer than four or more than four remotely controllable manipulator systems may be included as part of the patient-side cart 100. While in the depicted example, the base 110 includes casters to allow ease of mobility, in some implementations, the patient-side cart 100 is fixedly mounted to a floor, ceiling, operating table, structural framework, or the like.

Many of the exemplary manipulator assemblies described herein will have more degrees of freedom (DOFs) than needed to position and move an end effector within a surgical site. For example, an end effector that can be positioned with six DOFs at an internal surgical site through a minimally invasive aperture, in some implementations, has nine DOFs. These nine DOFs include, for example, six end effector DOFs, with three of these DOFs for location and three of these DOFs for orientation. These nine DOFs also include, for example, three DOFs to comply with the access site constraints. In certain implementations, additional DOFs are provided. Highly configurable manipulator assemblies having more DOFs than are needed for a given end effector position can be described as having or providing sufficient DOFs to allow a range of joint states for an end effector pose in a workspace. For example, for a given end effector position, the manipulator may occupy (and be driven between) any of a range of alternative manipulator linkage positions. Similarly, for a given end effector velocity vector, the manipulator may have a range of differing joint movement speeds for the various joints of the manipulator.

When used for minimally invasive robotic surgery, movement of the manipulator systems 120, 130, 140, 150 may be controlled by a controller of the system so that a shaft or intermediate portion of instruments mounted to the manipulator systems 120, 130, 140, 150 are constrained to safe motions through minimally invasive surgical access sites or other apertures. Such motion may include, for example, axial insertion of a shaft through an aperture site, rotation of the shaft about its axis, and pivotal motion of the shaft about a pivot point adjacent the access site. In some cases, excessive lateral motion of the shaft that might otherwise tear the tissues adjacent the aperture or enlarge the access site inadvertently is inhibited. Some or all of such constraint on the motions of the manipulator systems 120, 130, 140, 150 at the access sites may be imposed using mechanical manipulator joint linkages that inhibit improper motions, or may in part or in full be imposed using robotic data processing and control techniques. Hence, such minimally invasive aperture-constrained motion of the manipulator may employ between zero and three DOFs of the manipulator.

In some examples, a first manipulator system and a second manipulator system of the manipulator systems 120, 130, 140, 150 hold instruments, and a third manipulator system of the manipulator systems 120, 130, 140, 150 holds an image capturing device such as a monoscopic or stereoscopic endoscope. In this example, the remaining, fourth manipulator system is available so that another instrument may be introduced at the work site. Alternatively, the remaining manipulator system may be used for introducing a second endoscope or another image capturing device, such as an ultrasound transducer, to the work site.

Each of the manipulator systems 120, 130, 140, and 150 is formed of links that are coupled together and manipulated through actuatable joints. Each of the manipulator systems 120, 130, 140, and 150 includes a setup assembly and a device manipulator. The setup assembly positions its held device so that a pivot point occurs at its entry aperture into the patient. The device manipulator may then manipulate its held device so that it may be pivoted about the pivot point, inserted into and retracted out of the entry aperture, and rotated about its shaft axis.

Figure 2:
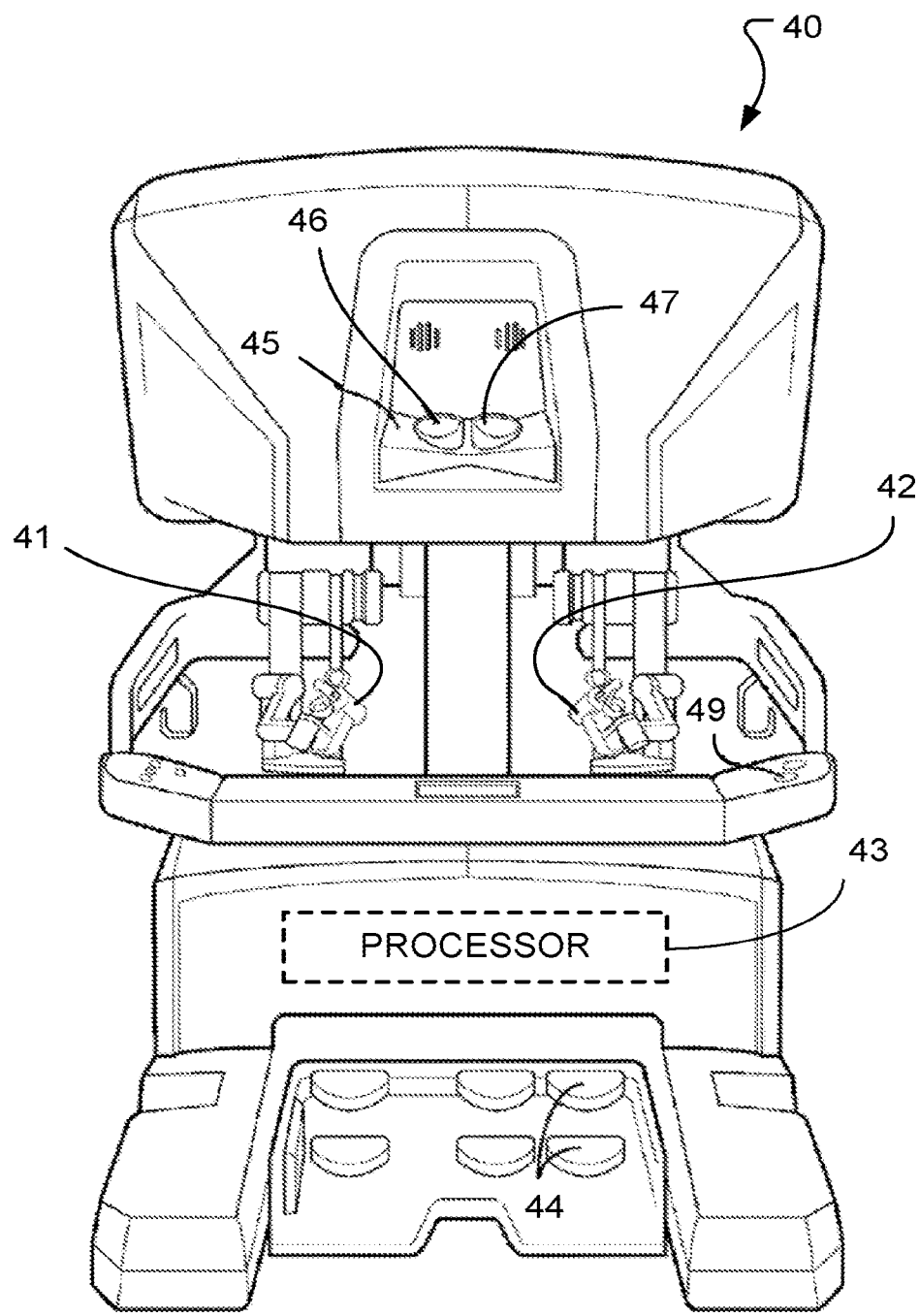
FIG. 2 is a front view of an example operator console of a computer-assisted tele-operated system.

In the depicted example, the operator console 40 shown in FIG. 2 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The operator console 40 also includes left and right input devices 41, 42 that the user may grasp respectively with his/her left and right hands to manipulate devices (e.g., instruments) being held by the manipulator systems 120, 130, 140, and 150 of the patient-side cart 100 in preferably six DOFs. Foot pedals 44 with toe and heel controls are provided on the operator console 40 so the user may control movement and/or actuation of devices associated with the foot pedals.

A processor 43 is provided in the operator console 40 for control and other purposes. The processor 43 performs various functions in the medical robotic system. In some examples, the processor 43 is operable to translate and transfer the mechanical motion of input devices 41, 42 to actuate their respective joints in their associated manipulator systems 120, 130, 140, and 150 so that the operator can manipulate devices, such as the instruments, from a remote location of the operator console 40. The processor 43 can also be configured to implement the methods, cross-coupling control logic, and controllers described herein.

It is to be appreciated that the processor 43 may be implemented by any combination of hardware, software and firmware. Also, its functions as described herein may be performed by one unit or divided up among a number of subunits, each of which may be implemented in turn by any combination of hardware, software and firmware. Further, although being shown as part of or being physically adjacent to the operator console 40, the processor 43 may also be distributed as subunits throughout the telesurgery system.

Figure 1B:
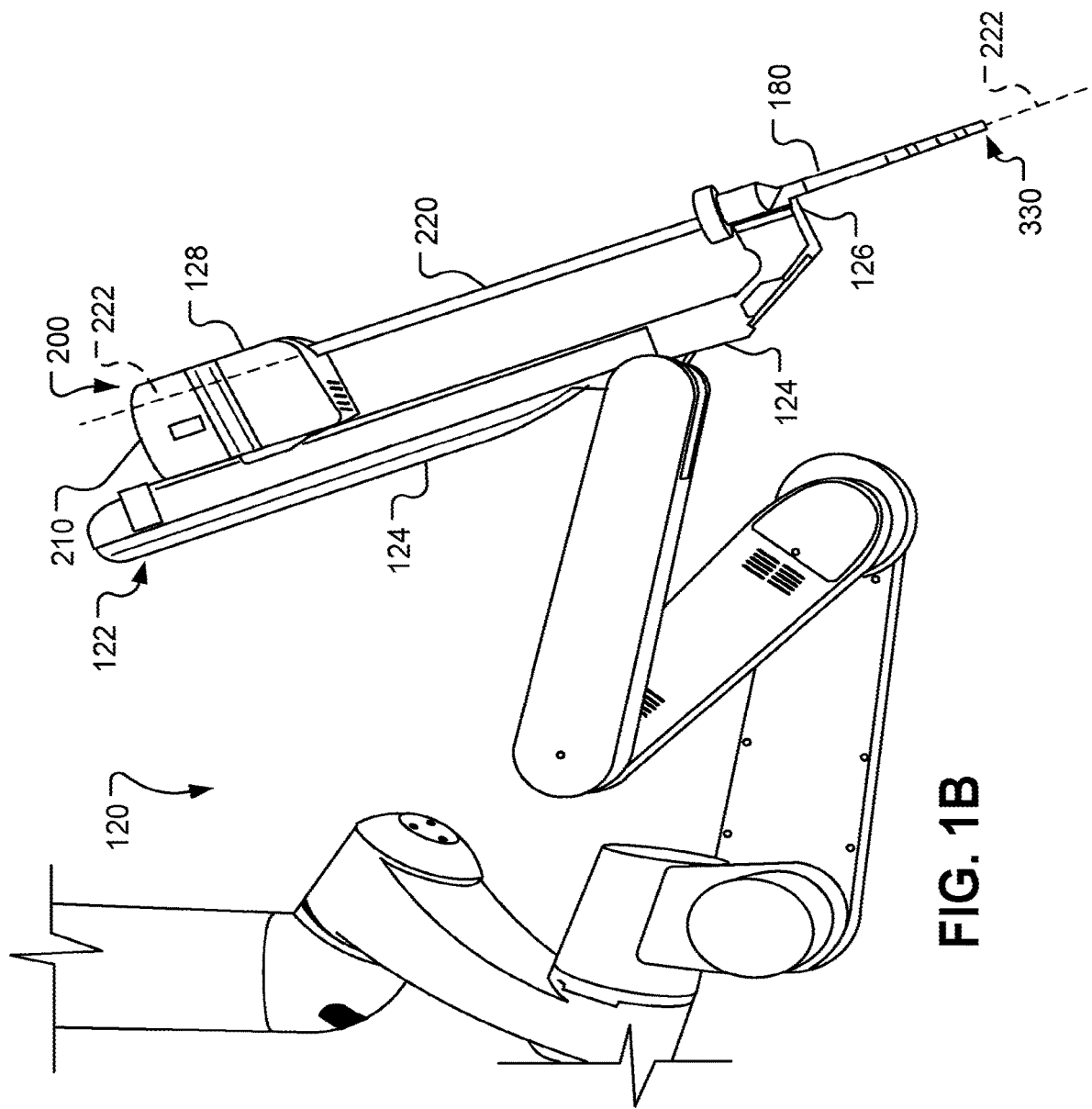
FIG. 1B is a side view of an example manipulator system of a computer-assisted tele-operated system.

Referring also to FIG. 1B, the manipulator systems 120, 130, 140, and 150 can manipulate devices such as instruments to perform tasks such as those associated with minimally invasive surgery. For example, in the depicted arrangement the manipulator system 120 is pivotably coupled to an instrument holder 122. A cannula 180 and an instrument 200 and are, in turn, releasably coupled to the instrument holder 122. The cannula 180 is a tubular member that is located at the patient interface site during a surgery. The cannula 180 defines a lumen in which an elongate instrument shaft 302 of the instrument 200 is slidably disposed. As described further below, in some implementations, the cannula 180 includes a distal end portion with a body wall retractor member.

The instrument holder 122 is pivotably coupled to a distal portion (e.g. a distal link, a distal end portion such as a distal end, etc.) of the manipulator system 120. In some implementations, the pivotable coupling between the instrument holder 122 and the distal portion of manipulator system 120 is a motorized joint that is actuatable from the operator console 40 and processor 43.

The instrument holder 122 includes an instrument holder frame 124, a cannula clamp 126, and an instrument holder carriage 128. The cannula clamp 126 is fixed to a distal portion (e.g. a distal end or some other distal portion) of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some implementations, the movement of the instrument holder carriage 128 along the instrument holder frame 124 is a motorized, translational movement that is controllable by the processor 43.

The instrument 200 includes a transmission assembly 210, the shaft 302, and an end effector 330. The transmission assembly 210 is configured to be releasably coupled with the instrument holder carriage 128. The shaft 302 extends distally from the transmission assembly 210. The end effector 330 is disposed at a distal portion (e.g. a distal end or some other distal portion) of the shaft 302. The end effector 330 can move in the workspace with between two and six DOFs.

The shaft 302 defines a longitudinal axis 222 that is coincident with a longitudinal axis of the cannula 180. As the instrument holder carriage 128 translates along the instrument holder frame 124, the shaft 302 of the instrument 200 is moved along the longitudinal axis 222. In such a manner, the end effector 330 can be inserted and/or retracted from a surgical workspace within the body of a patient.

Figure 3:
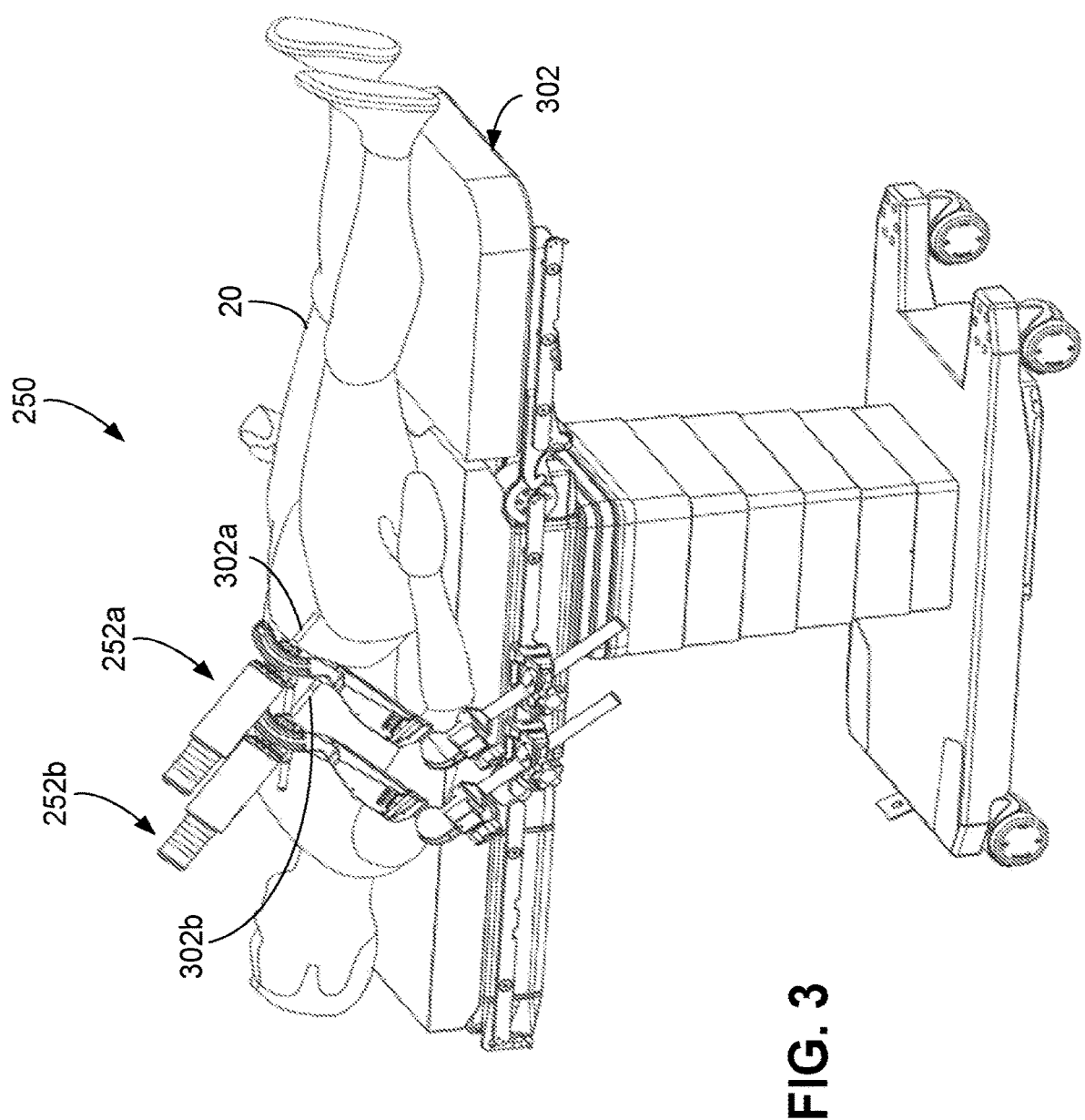
FIG. 3 is a perspective view of another example of a patient-side computer-assisted tele-operated system.

FIG. 3 is perspective view of another example of a patient-side system 250 that can be used for procedures such as minimally invasive computer-assisted tele-operated surgery. A patient 20 is supported on an operating table 10. The patient-side system 250 includes a first manipulator system 252a and a second manipulator system 252b that are each mounted to the operating table 10. In some cases, this configuration of patient-side system 250 can be used as an alternative to the patient-side cart 100 of FIG. 1. While only two manipulator systems 252a and 252b are depicted, it should be understood that more than two (e.g., three, four, five, six, and more than six) can be included in some configurations.

In some cases, the operating table 10 may be moved or reconfigured during the surgery. For example, in some cases, the operating table 10 may be tilted about various axes, raised, lowered, pivoted, rotated, and the like. In some cases, such movements of the operating table 10 may be integrated as a part of the computer-assisted tele-operated surgery system, and controlled by the system.

The manipulator systems 252a, 252b are driven to move instruments 300a, 300b within the operating environment (e.g. a surgical environment in the case of surgery), e.g., relative to the patient 20. As described herein with respect to FIG. 4, in some implementations, the manipulator systems 252a, 252b include remotely operable powered joints that, when driven, reposition and reorient the instruments 300a, 300b such that the instruments 300a, 300b can be placed in desired poses during a surgical procedure.

Figure 4:
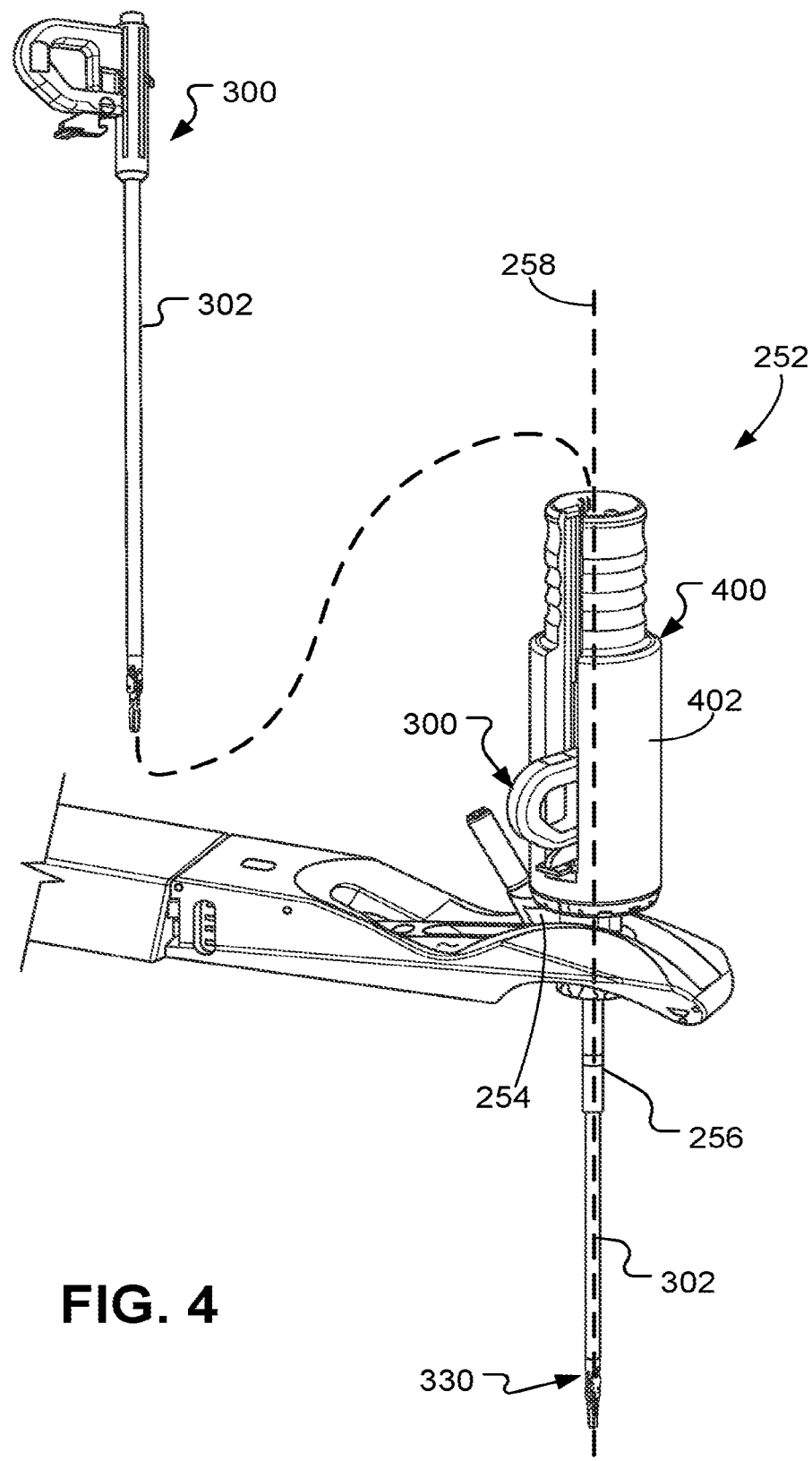
FIG. 4 is a perspective view of an example manipulator system of a computer-assisted tele-operated system.

FIG. 4 depicts a perspective view of a manipulator portion of a manipulator system 252, e.g., the manipulator system 252a or the manipulator system 252b, and an instrument 300 to be mounted to the manipulator system 252. The manipulator system 252 includes an instrument drive system coupling 254 to releasably couple with an instrument drive system 400 to which the instrument 300 is mounted. In particular, the coupling 254 is configured to releasably couple with a housing 402 of the drive system 400. The coupling 254 is also configured to releasably couple with a patient body wall access cannula 256 that is coaxial with an insertion axis 258 of the instrument 300. The cannula 256 defines a lumen that slidably receives a shaft 302 of the instrument 300 (or of other devices such as, but not limited to, an endoscope) along the insertion axis 258. During a surgical operation, the cannula 256 extends distally from the coupling 254 through the patient via a surgical access location on the patient body wall.

The drive system 400 releasably receives the instrument 300. In particular, the instrument 300 is inserted through the housing 402 of the instrument 300 and extends through the housing 402 into the cannula 256. The drive system 400 is, for example, detachable from the manipulator system 252 to enable the drive system 400 to be easily interchanged with another actuator system. When the instrument 300 is mounted to the drive system 400, the shaft 302 of the instrument 300 extends through the cannula 256. The cannula 256 extends through the patient body wall to guide the shaft 302 and an end effector 330 of the instrument 300 through the patient body wall into a cavity where the end effector 330 is to perform the surgical operation. The end effector 330 is remotely controlled by the surgeon 202 (shown in FIG. 2) when the computer-assisted tele-operated surgery is performed.

The drive system 400 is, for example, a standalone unit including a system of drive mechanisms housed in the housing 402. The drive mechanisms are operated to control motion of the instrument 300 in multiple DOFs when the instrument 300 is mounted to the drive system 400. In some examples, the motions of the instrument 300 controllable by the drive mechanisms include a motion of part or all of the instrument 300 relative to the housing 402 of the drive system 400. The motions can also include a motion of the end effector 330 of the instrument 300. The manipulator system 252 drives the coupling 254 to control motion of the drive system 400 and the instrument 300 mounted to the drive system 400. The drive mechanisms include actuators to drive the actuation engagement members of the instrument 300, as described herein.

To control the motion of the instrument 300, the surgeon provides inputs using the operator console 40 as described in reference to FIG. 2 to generate control signals to operate the actuators of the drive system 400. In one example, the manipulator system 252 includes actuators to control a first set of DOFs of the instrument 300, and the drive system 400 includes one or more actuators to control a second set of DOFs of the instrument 300. The first set of DOFs include, for example, a pitch motion, a yaw motion, and a roll motion of the instrument 300 relative to the patient 20. The instrument 300 is configured to undergo the pitch motion, the yaw motion, and the roll motion when the instrument 300 is mounted to the drive system 400 and the drive system 400 is mounted to the coupling 254. The second set of DOFs of the instrument 300 include, for example, an insertion motion of the instrument 300 and an end effector motion of the end effector 330. In some examples, the insertion motion corresponds to a translation of the instrument 300 in its entirety along the longitudinal axis. In some examples, the insertion motion corresponds to a translation of a part of the instrument 300 along the longitudinal axis. In some examples, the manipulator system 252 does not include an actuator to cause actuation of the insertion motion or to actuate the end effector 330. Rather, the drive system 400 includes these actuators, and the drive system 400 can be disconnected from the manipulator system 252 to enable different actuation modules to be easily mounted to the manipulator system 252.

Example End Effectors

Figure 5:
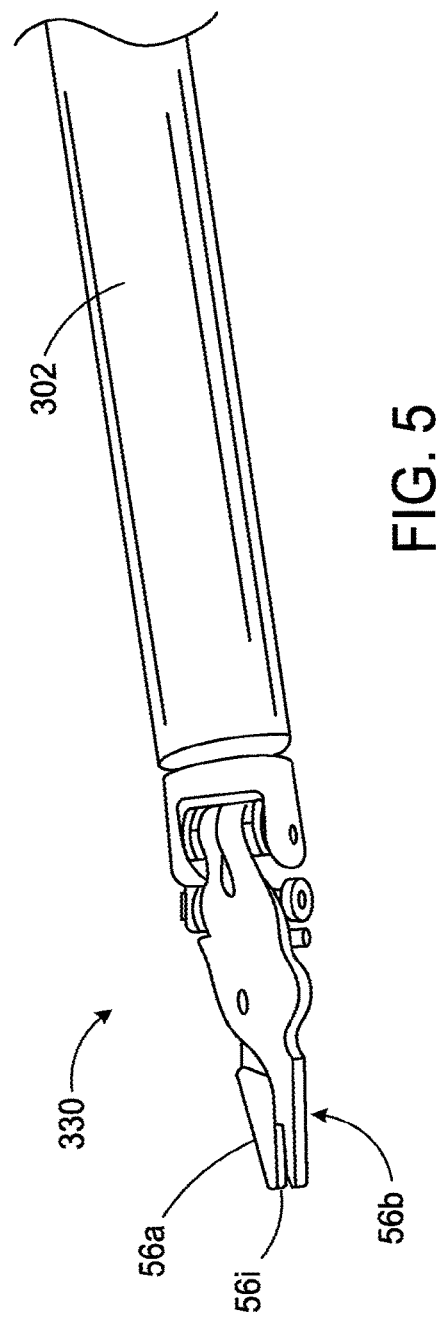
FIG. 5 is a perspective view of a distal end portion of an example instrument in a first configuration.
Figure 6:
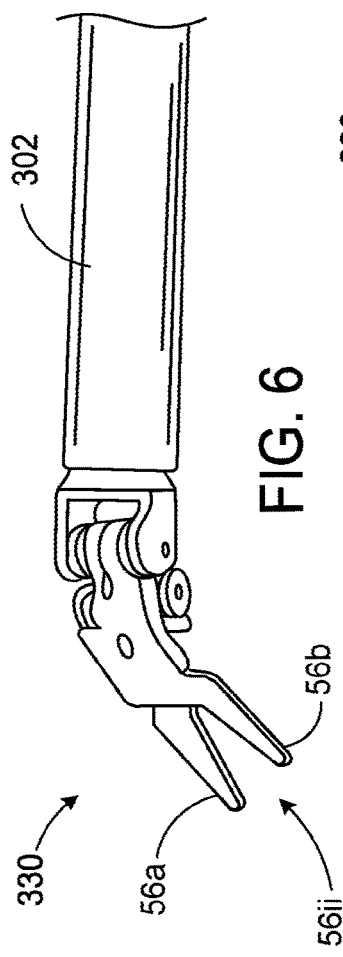
FIG. 6 is a perspective view of the distal end portion of the instrument of FIG. 5 in a second configuration.
Figure 7:
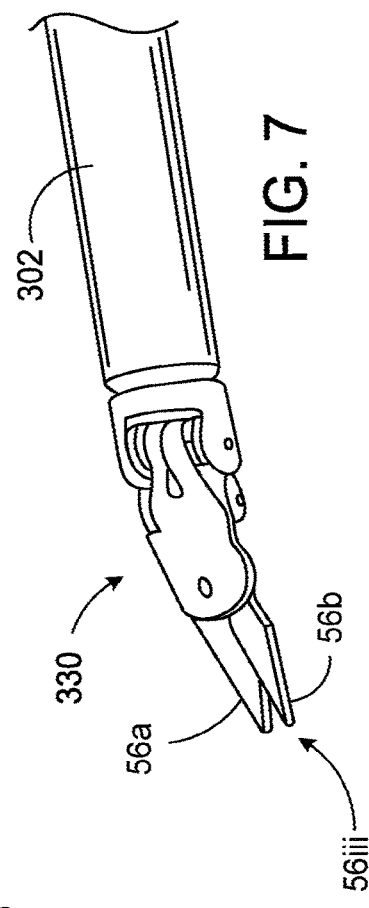
FIG. 7 is a perspective view of the distal end portion of the instrument of FIG. 5 in a third configuration.

Referring to FIGS. 5-7, the end effector motion of the second set of DOFs can vary between implementations. FIGS. 5-7 depict a variety of alternative computer-assisted tele-operated instruments of different types and differing end effectors 330 may be used, with the instruments of at least some of the manipulators being removed and replaced during a procedure. FIGS. 5-7 show instruments useful for a medical procedure such as a surgical procedure, and other non-surgical or non-medical instruments are contemplated. Several of these end effectors shown in FIGS. 5-7, including, for example, DeBakey Forceps 56i, microforceps 56ii, and Potts scissors 56iii include first and second end effector elements 56a, 56b which pivot relative to each other so as to define a pair of end effector jaws. Other end effectors, including scalpels and electrocautery probes, have a single end effector element. For instruments having end effector jaws, the end effector motion includes a clamping motion of the jaws. The jaws will often be actuated by squeezing the grip members of input devices 41, 42.

In some cases, the computer-assisted tele-operated instruments include multiple DOFs such as, but not limited to, roll, pitch, yaw, insertion depth, opening/closing of jaws, actuation of staple delivery, activation of electro-cautery, and the like. At least some of such DOFs can be actuated by an instrument drive system to which the instrument can be selectively coupled. While the descriptions of FIGS. 8-14 indicate that the second set of DOFs facilitated by the drive system 400 includes two DOFs with one of the DOFs being an insertion DOF and the other of the DOF being an end effector pitch DOF, in some implementations, additional DOFs are facilitated by the drive system 400. The end effector motion can include multiple modes of motion, e.g., motion in multiple DOFs. The end effector is, for example, movable in two or more of a roll motion, a pitch motion, a yaw motion, and/or a clamping motion. The end effector is further movable along a longitudinal axis of the instrument 300 in the insertion motion.

In some implementations, the computer-assisted tele-operated instruments include end effectors with two individually movable components such as, but not limited to, opposing jaws designed for grasping or shearing. When a first one of the individually movable components is moved as a second one of the individually movable components remains generally stationary or is moved in an opposing manner, the end effector can perform useful motions such as opening and closing for grasping, shearing, releasing, and the like. When the two components are moved synchronously in the same direction, speed and distance, the resulting motion is a type of pitch or yaw movement of the end effector. Hence, in some examples of instruments that have end effectors with two individually movable components, such as jaws, the arrangement can provide two DOFs (e.g., pitch/yaw movements and opening/closing movements).

In a medical application, the shaft 302 allow the end effector 330 and the distal end of the shaft 302 to be inserted distally into a medical worksite, such as a surgical worksite, through a minimally invasive aperture (via cannula 180), which may be through a body wall (e.g., abdominal wall), a natural orifice such as the mouth or anus, or the like. In some cases, a body wall retractor member on a distal portion (e.g. a distal end or some other distal portion) of the cannula 180 can be used to tent the body wall, thereby increasing the surgical workspace size. In some cases, a surgical worksite may be insufflated, and movement of the end effectors 330 within the patient will often be effected, at least in part, by pivoting of the instruments 200 about the location at which the shaft 302 passes through the minimally invasive aperture. In other words, the manipulator systems 120, 130, 140, and 150 will move the transmission assembly 210 outside the patient so that the shaft 302 extends through a minimally invasive aperture location so as to help provide a desired movement of end effector 50. Hence, the manipulator systems 120, 130, 140, and 150 will often undergo significant movement outside of the patient during a surgical procedure.

Example Instruments

Referring to FIG. 8, an example instrument 300 that can be used as part of a computer-assisted tele-operated surgery system is schematically depicted. The instrument 300 includes an instrument shaft 302 having a proximal end portion 310 and a distal end portion 320 opposite from the proximal end portion 310. The instrument 300 also includes an end effector 330. In this schematic diagram, the end effector 330 is depicted as having a single degree of freedom (DOF) in relation to the shaft 302 (i.e., a freedom to pan the end effector 330 in a rotary or pivoting fashion). It should be understood, however, that the end effectors 330 of the instruments described herein can have more than one DOF (e.g., two, three, four, five, six, or more than six DOFs). Moreover, it should be understood that the concepts described in the context of the single DOF of the end effector 330 can be extended to each DOF of multiple DOFs of the instrument 300 and of other types of instruments for computer-assisted tele-operated surgery systems.

Example instrument 300 also includes a first tensioning member 340, a first actuator engagement member 350, a second tensioning member 360, and a second actuator engagement member 370. The first tensioning member 340 and the second tensioning member 360 comprise a flexible tensioning member for the instrument 300. The first tensioning member 340 is coupled to the end effector 330 and extends along the shaft 302 where it terminates at the first actuator engagement member 350. Similarly, the second tensioning member 360 is coupled to the end effector 330 and extends along the shaft 302 where it terminates at the second actuator engagement member 370. The first actuator engagement member 350 and the second actuator engagement member 370 are movably coupled to the proximal end portion 310 of the instrument. In some implementations, the first actuator engagement member 350 and the second actuator engagement member 370 are slidably coupled to the proximal end portion 310 of the instrument.

In some implementations, some or all portions of the first tensioning member 340 and the second tensioning member 360 include flexible cables (e.g., without limitation, stranded tungsten cables). In some implementations, the first tensioning member 340 and the second tensioning member 360 are different portions of a single, continuous component, such as a single, continuous cable. In some implementations, the first tensioning member 340 and the second tensioning member 360 comprise components physically separate from each other, such as two or more separate cables. The first tensioning member 340 and the second tensioning member 360 may additionally or alternatively include other components such as, but not limited to, hypo-tubes.

The first tensioning member 340 and the second tensioning member 360 are each coupled to the end effector 330. In the depicted example, the first tensioning member 340 and the second tensioning member 360 are each coupled to the end effector 330 via a pulley 332 (which can be a capstan, crank arm, rotary drive member, etc.). Hence, a proximal movement of the first actuator engagement member 350 moves the second actuator engagement member 370 distally, and moves the end effector 330 in a first manner relative to the shaft 302. Conversely, a proximal movement of the second actuator engagement member 370 moves the first actuator engagement member 350 distally, and moves the end effector 330 in a second manner relative to the shaft 302.

The instrument 300 is depicted here as being separated from an instrument drive system. Accordingly, in some implementations, the tension in the first tensioning member 340 and the second tensioning member 360 can be less than the tension used during the operation of the instrument 300. In some cases, having a relatively low tension in the first tensioning member 340 and the second tensioning member 360 while the instrument 300 is not in use can be advantageous (e.g., to reduce the potential for cable stretch). In some implementations, pre-load tensioning members (e.g., springs, not shown) may be included in instrument 300 to maintain a minimal tension in the first tensioning member 340 and the second tensioning member 360 while the instrument 300 is separated from an instrument drive system. Such minimal pre-tensioning may help ensure that the first tensioning member 340 and the second tensioning member 360 remain oriented within the instrument 300 as desired.

While the instrument 300 is depicted as having a single DOF, it should be understood that this is a simplified schematic diagram and that the instrument 300 can have two or more DOFs. The concepts described herein in reference to the single DOF of instrument 300 (as depicted) can be extrapolated to the two or more DOFs of the instruments provided herein. For example, when the end effector 330 includes two individually movable components, such as opposing jaws designed for grasping or shearing as described above, the arrangement provides two DOFs (e.g., pitch/yaw movements when the components are moved synchronously and opening/closing movements when the components are moved asynchronously or in an opposing manner). Extending the concepts described in reference to the instrument 300 to such an end effector would result in an instrument having four actuator engagement members and four tensioning members to actuate the two DOFs.

Referring to FIG. 9A, the instrument 300 can be selectively coupled with an instrument drive system 400. That is, the instrument 300 can be coupled with the drive system 400 for operation as part of a computer-assisted tele-operated surgery system. Additionally, the instrument 300 can be uncoupled from the drive system 400 (e.g., for replacement by another type of instrument, for sterilization of the instrument 300, etc.).

In some implementations, the drive system 400 can be mounted to a manipulator, which can in turn be mounted to another structure or a base. The drive system 400 can be interchangeably mounted to a manipulator in some cases. That is, in some implementations, the drive system 400 is designed for convenient detachment from a manipulator such that it is readily interchangeable with another instrument drive system. In some implementations, the drive system 400 is interchangeable with other instrument drive systems. In some implementations, the drive system 400 is affixed to a manipulator in such a way that the drive system 400 is not readily detachable or interchangeable.

In some implementations, the instrument 300 is configured to be slidably coupled with the drive system 400. That is, the instrument 300 can be slidably extended distally and slidably retracted proximally in relation to the drive system 400.

The drive system 400 includes drive mechanisms that are configured to engage or couple with the engagement members of the instrument 300 and drive the engagement members. The drive mechanisms include actuators operable to drive the engagement members. In the depicted example, the drive system 400 includes a first drive mechanism including a first actuator 410, a second drive mechanism including a second actuator 420, and a third drive mechanism including a shaft actuator 430. In some implementations, the first, second, and/or third drive mechanisms include drivetrains to convert torques applied by the first, second, and third actuators 410, 420, 430 into forces on, or longitudinal translation of, the engagement members 350, 360, 370 of the instrument 300. The first actuator 410 is configured to be releasably coupled with the first actuator engagement member 350. When thus coupled, the first actuator 410 can induce a tensile force in the first tensioning member 340. The second actuator 420 is configured to be releasably coupled with the second actuator engagement member 370. When thus coupled, the second actuator 420 can induce a tensile force in the second tensioning member 360. The first, second, and third drive mechanisms, for example, include lead screws that can be rotated to apply forces, or cause motion, parallel to the longitudinal axis of the instrument 300 when the first, second, and third actuators 410, 420, 430 are driven.

In light of the arrangement between the instrument 300 and the first and second actuators 410 and 420 of the drive system 400 as described above, it can be envisioned that concerted modulation of the forces exerted from the first and second actuators 410 and 420 to the first and second actuator engagement members 350 and 370, respectively, can result in controlled motion of the end effector 330 along its DOF. Moreover, it can also be envisioned (as described further below), that the tensions in the first and second tensioning members 340 and 360 can also be controlled by the concerted modulation of the forces exerted from the first and second actuators 410 and 420 to the first and second actuator engagement members 350 and 370, respectively. Still further, it can also be envisioned that the tensions in the first and second tensioning members 340 and 360 can be controlled by the concerted modulation of the forces exerted from the first and second actuators 410 and 420 to the first and second actuator engagement members 350 and 370, respectively, while the concerted modulation of the forces exerted from the first and second actuators 410 and 420 to the first and second actuator engagement members 350 and 370 also concurrently cause desired movements of the end effector 330. In this way, the tensions in the first and second tensioning members 340 and 360 can be controlled to a desired amount of tensile force while movements of the end effector 330 are being made as desired. This concept can be referred to herein as "dynamic tension control."

Still referring to FIG. 9A, the drive system 400 also includes the third drive mechanism including the shaft actuator 430. The shaft actuator 430 can releasably couple with the shaft 302. In some implementations, the shaft actuator 430 can releasably couple with the shaft 302 (or to a structure coupled to the shaft 302) using a latch mechanism. Accordingly, in some such implementations, while the shaft actuator 430 is latched or otherwise physically coupled to the shaft 302, the shaft actuator 430 is able to drive the shaft 302 by applying one or more forces or torques to the shaft 302. In some such implementations the shaft actuator 430 is able to exert a distally-directed force or a proximally-directed force to the shaft 302. When the forces applied by the shaft actuator 430 is sufficient to overcome other forces experienced by the shaft 302, the forces applied by the shaft actuator 430 can distally extend or proximally retract the instrument 300 in relation to the drive system 400.

The actuators 410, 420, and 430 can be various types of actuators. Example actuator types include electrical actuators, hydraulic actuators, pneumatic actuators, magnetic actuators, light actuators, etc. Thus, although many of the example actuators discussed herein can be motors, same Or analogous techniques can utilize actuators based on other technologies. In some implementations, the first actuator 410, a second actuator 420, and a shaft actuator 430 each includes electrical motors that are coupled to lead screws that linearly drive nut members on the threads of the lead screw. In some implementations, the entire assembly of the instrument 300 in combination with the drive system 400 can be driven together to result in a desired motion of the end effector, such as a rolling motion about the longitudinal axis of the instrument 300.

Figure 9B:
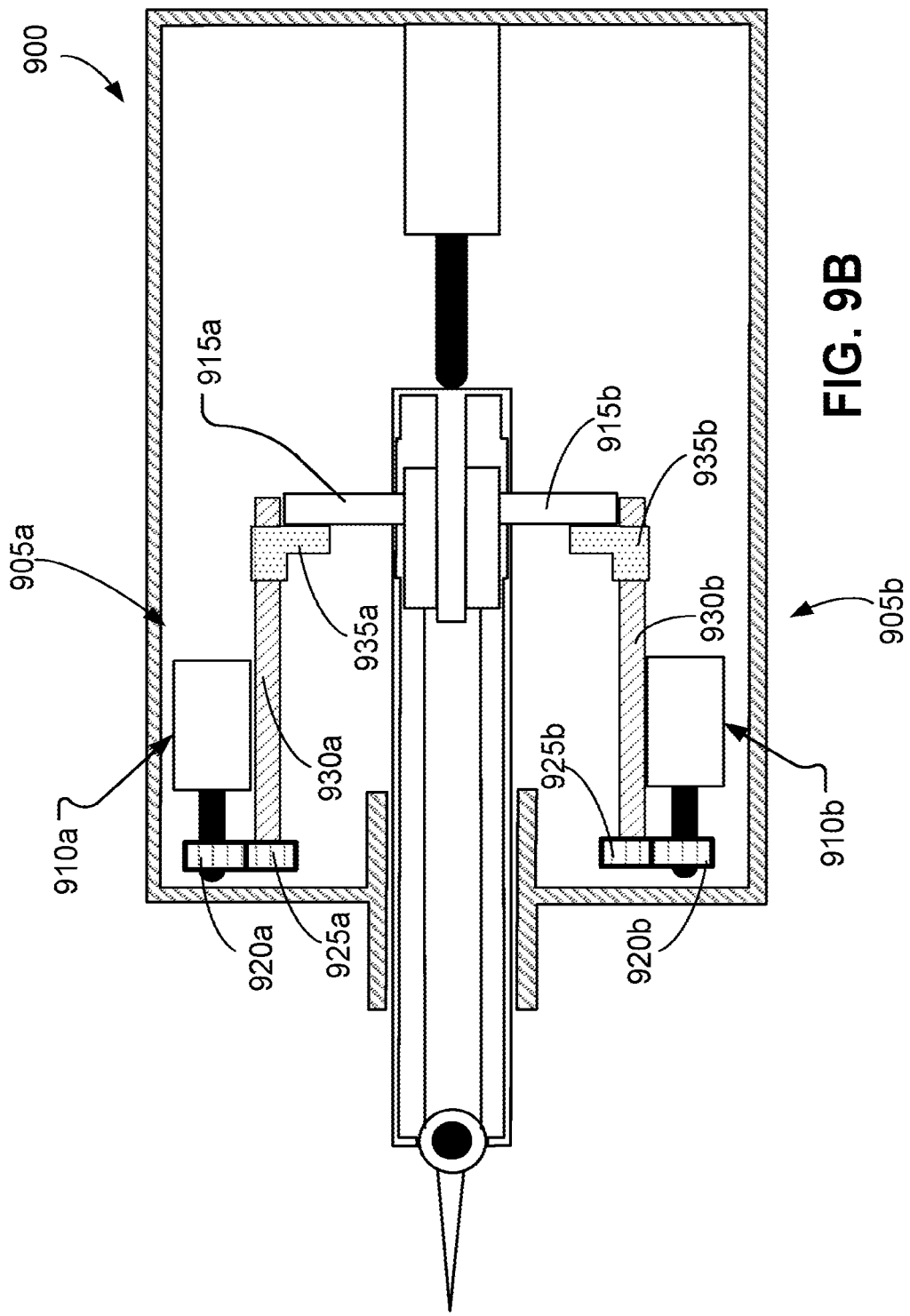
FIG. 9B is a schematic diagram of the tele-operated instrument of FIG. 8 coupled with another example instrument drive system.

FIGS. 10-14 are described with respect to the example drive system 400 of FIG. 9A. However, other implementations are possible, including the implementations described with respect to FIG. 9B and others. Referring to FIG. 9B, an instrument 900 differs from the instrument 300 in that drive mechanisms 905a, 905b include actuators 910a, 910b as well as additional drivetrain components to move engagement members 915a, 915b. In particular, the drive mechanisms 905a, 905b include gears 920a, 920b mounted to the actuators 910a, 910b, which are rotary actuators. The gears 920a, 920b are engaged to gears 925a, 925b fixed to lead screws 930a, 930b. As the lead screws 930a, 930b rotate in response to rotation of the actuators 910a, 910b, the lead screws 930a, 930b translate longitudinally to cause abutting members 935a, 935b to translate and move the engagement members 915a, 915b. FIGS. 9A and 9B depict some examples of different possible drive mechanisms. Other drive mechanisms that facilitate linear motion of the engagement members 915a, 915b are possible.

Referring also to FIG. 10, a force diagram 500 can be used to further describe the structure and operations of the instrument 300 in combination with the drive system 400. The body 301 is representative of the instrument 300. Force F1 is representative of the force applied by the first actuator 410 to the first engagement member 350. Force F2 is representative of the force applied by the second actuator 420 to the second engagement member 370. Force FS is representative of the force applied by the shaft actuator 430 to the shaft 302.

Force FS is directionally opposite to forces F1 and F2. Hence, in a static context, force FS is equal to the sum of forces F1 and F2. In a dynamic context, if force FS is greater than the sum of forces F1 and F2, then the body 301 will move in the direction of force FS. Conversely, if force FS is less than the sum of forces F1 and F2, then the body 301 will move in the direction of forces F1 and F2.

Applying the principles described above regarding the force diagram 500 to the analogous arrangement of the instrument 300 in combination with the drive system 400, the following concepts can be envisioned. While the instrument 300 is in a constant spatial relationship with the drive system 400 (i.e., in a static context), the sum of the forces exerted from the first and second actuators 410 and 420 to the first and second actuator engagement members 350 and 370 equal the force exerted from the shaft actuator 430 to the shaft 302. In addition, while the sum of the forces exerted from the first and second actuators 410 and 420 to the first and second actuator engagement members 350 and 370 are greater than the force exerted from the shaft actuator 430 to the shaft 302, the instrument 300 will move proximally in relation to the drive system 400. Still further, while the sum of the forces exerted from the first and second actuators 410 and 420 to the first and second actuator engagement members 350 and 370 are less than the force exerted from the shaft actuator 430 to the shaft 302, the instrument 300 will move distally in relation to the drive system 400.

In general, the combinations of forces from the actuators 410, 420, and 430 that cause the proximal and distal movements of the instrument 300 in relation to the drive system 400 involve the sum of the forces exerted from the first and second actuators 410 and 420 to the first and second actuator engagement members 350 and 370. Hence, it can be envisioned that the forces exerted from the first and second actuators 410 and 420 to the first and second actuator engagement members 350 and 370 can be equal to each other, or can differ from each other while the sum of the forces is still a total amount that is appropriate to result in a desired distal/proximal movement and/or orientation between the instrument 300 and the drive system 400. For example, in the case when the forces exerted from the first and second actuators 410 and 420 to the first and second actuator engagement members 350 and 370 differ from each other, a movement of end effector 330 will result, and in the case when the forces exerted from the first and second actuators 410 and 420 to the first and second actuator engagement members 350 and 370 are equal to each other, the end effector 330 will be stationary in relation to the shaft 302. Again, it should be understood that, using the structure and operational concepts provided herein, distal/proximal movements of the instrument 300 in relation to the drive system 400 can be made concurrently with movements of the end effector 330 in relation to the shaft 302. Moreover, both such movements can be made concurrently while the tensions in the first tensioning member 340 and the second tensioning member 360 are maintained at a desired level of tensile force (e.g., within a target range of desired tensile force).

Figure 11:
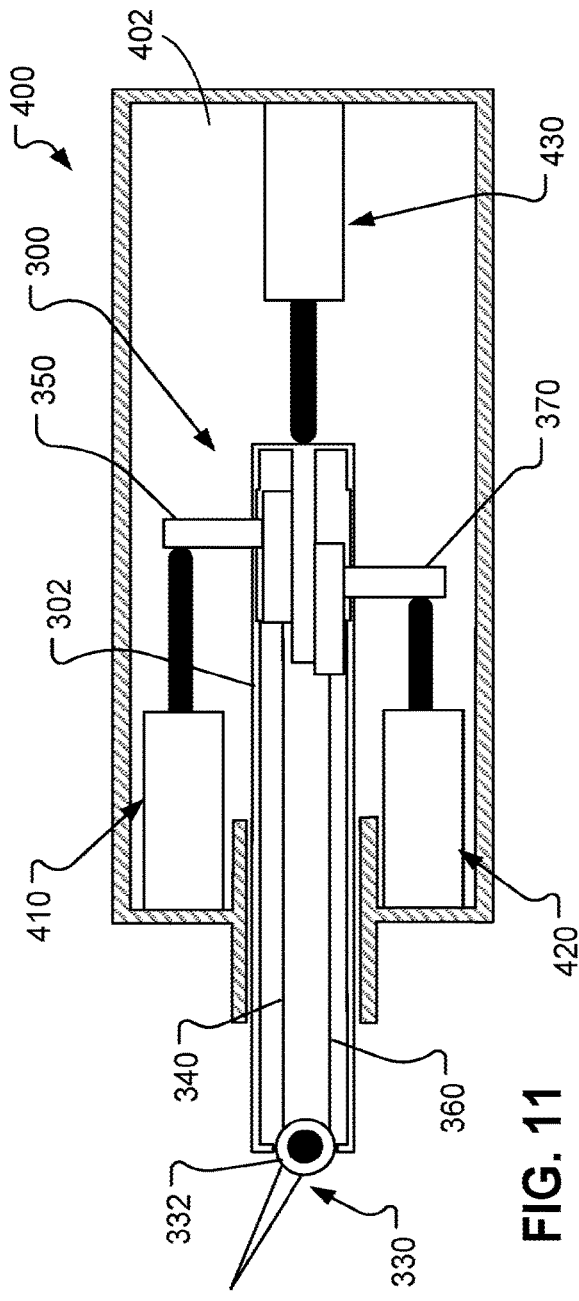
FIG. 11 is a schematic diagram of the instrument and drive system of FIG. 9A with the end effector oriented in an example pose.
Figure 12:
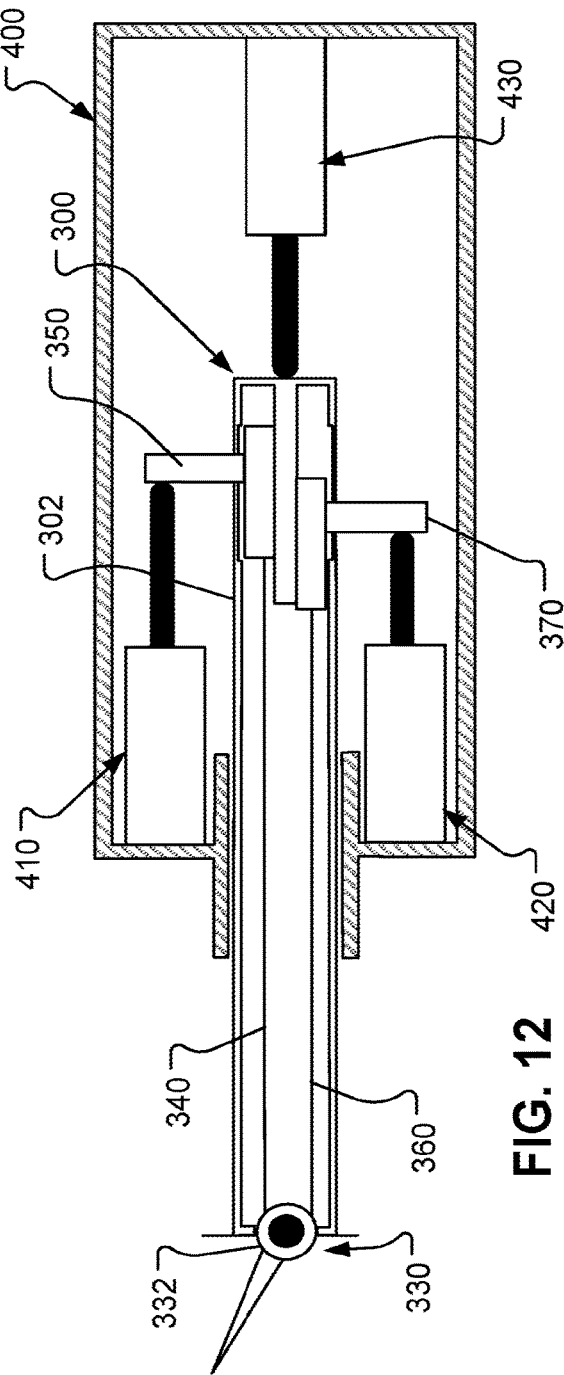
FIG. 12 is a schematic diagram of the instrument and drive system of FIG. 11 with the instrument extended distally in relation to the drive system while the end effector remains oriented in the example pose.
Figure 13:
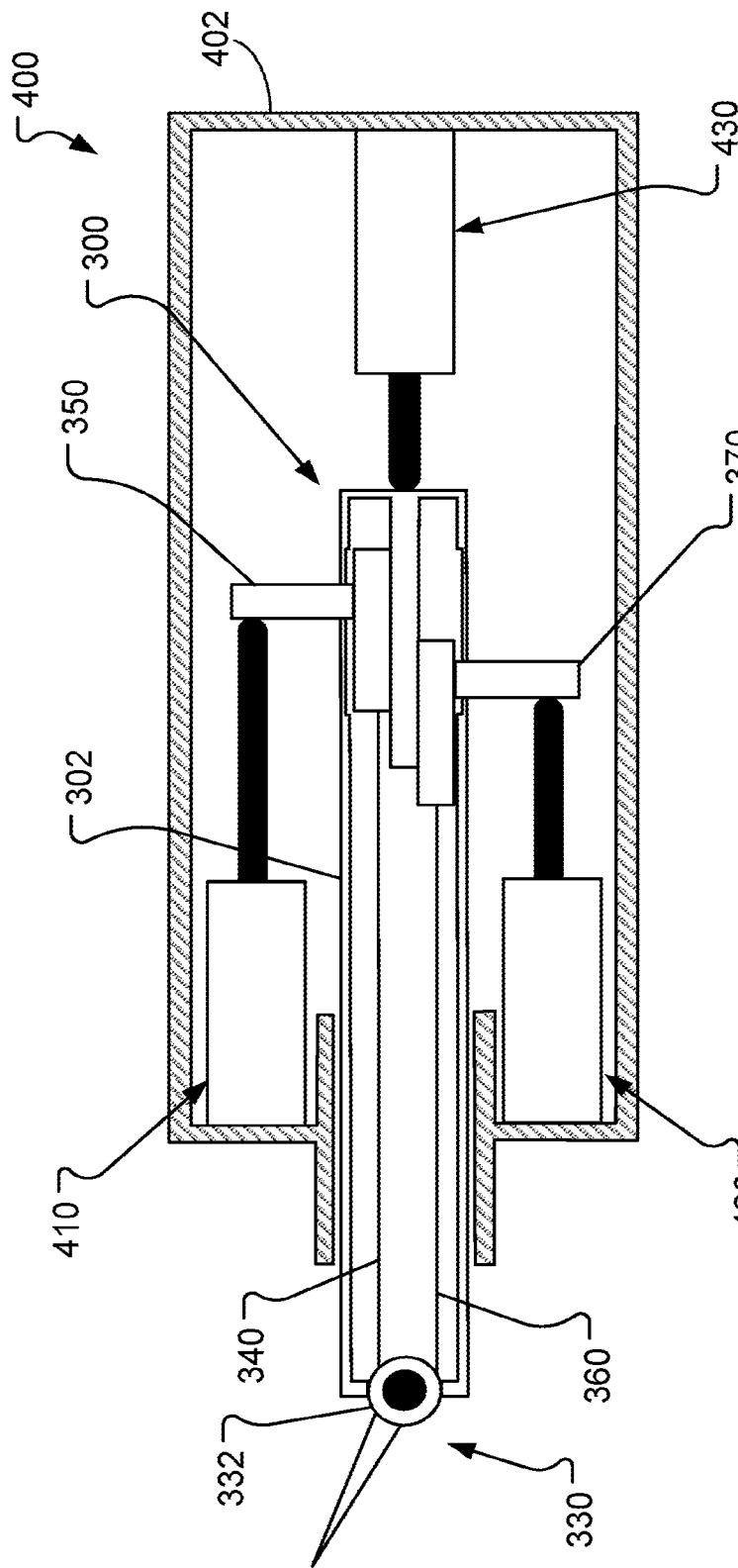
FIG. 13 is a schematic diagram of the instrument and drive system of FIG. 11 with the instrument retracted proximally in relation to the drive system while the end effector remains oriented in the example pose.

Referring also to FIGS. 11-13, the concepts described above can be further described by examples using illustrations of the instrument 300 in various orientations in relation to the drive system 400.

In a first example, the arrangement of FIG. 9A can be transitioned to that of FIG. 11 by temporarily increasing the force exerted by the first actuator 410 to the first actuator engagement member 350 in comparison to the force exerted by the second actuator 420 to the second actuator engagement member 370, while the sum of the two forces is held equal to the force exerted by the shaft actuator 430 to the shaft 302. In result, the second actuator engagement member 370 moves distally relative to the first actuator engagement member 350, and the end effector 330 moves in relation to the shaft 302 while the instrument 300 is maintained in a constant spatial relationship (i.e., no distal and proximal movements) in relation to the drive system 400. Such a movement can be made while the tensions in the first tensioning member 340 and the second tensioning member 360 are maintained at a desired level of tensile force (e.g., within a target range of desired tensile force).

In a second example, the arrangement of FIG. 9A can be transitioned to that of FIG. 12 by temporarily increasing the force exerted by the first actuator 410 to the first actuator engagement member 350 in comparison to the force exerted by the second actuator 420 to the second actuator engagement member 370, while the sum of the two forces is temporarily less than the force exerted by the shaft actuator 430 to the shaft 302. In result, both the first and second actuator engagement members 350, 370 move distally. In addition, the end effector 330 moves in relation to the shaft 302, and the instrument 300 extends distally in relation to the drive system 400. Such movements can be made while the tensions in the first tensioning member 340 and the second tensioning member 360 are maintained at a desired level of tensile force (e.g., within a target range of desired tensile force).

In a third example, the arrangement of FIG. 9A can be transitioned to that of FIG. 13 by temporarily increasing the force exerted by the first actuator 410 to the first actuator engagement member 350 in comparison to the force exerted by the second actuator 420 to the second actuator engagement member 370, while the sum of the two forces is temporarily greater than the force exerted by the shaft actuator 430 to the shaft 302. In result, the actuator engagement members 350, 370 move proximally. In addition, the end effector 330 moves in relation to the shaft 302, and the instrument 300 retracts proximally in relation to the drive system 400. Such movements can be made while the tensions in the first tensioning member 340 and the second tensioning member 360 are maintained at a desired level of tensile force (e.g., within a target range of desired tensile force).

In a fourth example, the arrangement of FIG. 12 can be transitioned to that of FIG. 13 by maintaining equal forces exerted by the first actuator 410 to the first actuator engagement member 350 and by the second actuator 420 exerted to the second actuator engagement member 370, while the sum of the two forces is temporarily greater than the force exerted by the shaft actuator 430 to the shaft 302. In result, the end effector 330 will not move in relation to the shaft 302, and the instrument 300 will retract proximally in relation to the drive system 400. Such a movement can be made while the tensions in the first tensioning member 340 and the second tensioning member 360 are maintained at a desired level of tensile force (e.g., within a target range of desired tensile force).

In a fifth example, the arrangement of FIG. 13 can be transitioned to that of FIG. 12 by maintaining equal forces exerted by the first actuator 410 to the first actuator engagement member 350 and by the second actuator 420 exerted to the second actuator engagement member 370, while the sum of the two forces is temporarily less than the force exerted by the shaft actuator 430 to the shaft 302. In result, the end effector 330 will move in relation to the shaft 302, and the instrument 300 will extend distally in relation to the drive system 400. Such a movement can be made while the tensions in the first tensioning member 340 and the second tensioning member 360 are maintained at a desired level of tensile force (e.g., within a target range of desired tensile force).

Figure 14:
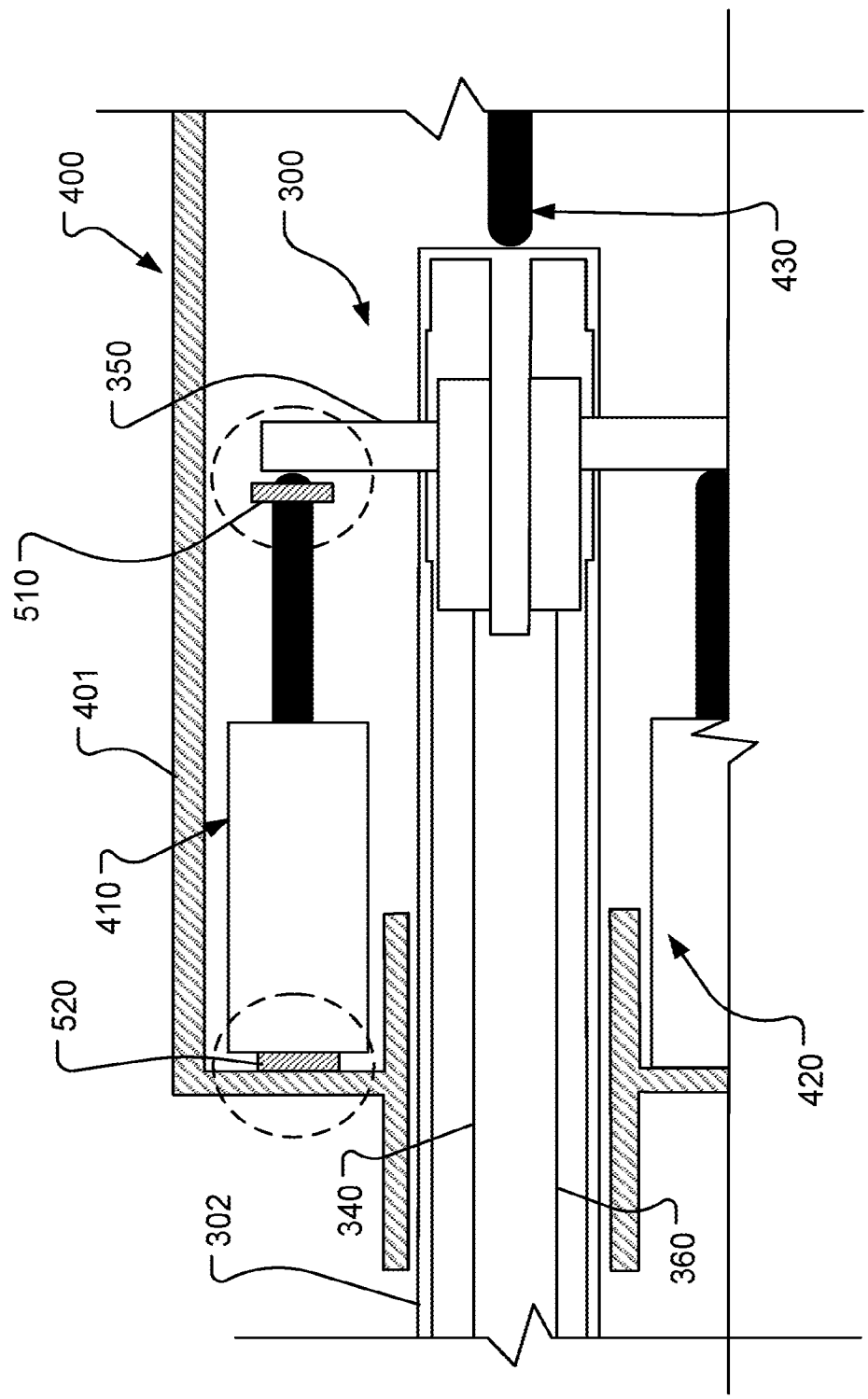
FIG. 14 is a schematic diagram of a portion of the instrument and drive system of FIG. 11 showing example locations of load cells for detecting forces such as cable tension.

Referring to FIG. 14, in some implementations, the forces exerted by the actuators 410, 420, and/or 430 to the instrument 300 can be detected by the use of one or more sensors. Output signals from these sensors can be used for controlling the actuators 410, 420, and/or 430 (i.e., to control movements of the instrument 300 and/or to control tensions of the first and second tensioning members 340 and 360).

In some implementations, a sensor 510 disposed near the juncture between the first actuator 410 and the first actuator engagement member 350. The sensor 510 is, for example, a load cell. A sensor 520 disposed near the juncture between the first actuator 410 and a structural member 401 of the drive system 400. The sensor 520 is also, for example, a load cell. The drive system 400 can be readily interchangeable in relation to mounting on a manipulator.

In some implementations, other devices can be used to detect the forces exerted by the actuators 410, 420, and/or 430 to the instrument 300. For example, in some implementations, strain gauges can be located on the actuator engagement members, e.g., the first actuator engagement member 350. In another example, the electrical current drawn by electric motors of the actuators 410, 420, and/or 430 can be measured and used as an indication of the forces exerted by the actuators 410, 420, and/or 430 to the instrument 300. In some implementations, a combination of such sensors and techniques can be used.

While the sensors 510, 520 are coupled to the first actuator 410 and/or the first actuator engagement member 350, in some implementations, the drive system 400 and/or the instrument 300 further includes sensors coupled to the second actuator 420 and/or sensors coupled to the third actuator 430. The combination of sensors present can enable forces and torques applied by each actuator 410, 420, 430 to be determined. Furthermore, while described as load cells, in some implementations, additional or alternative sensors may be present. The sensors include, for example, position sensors, pressure sensors, torque sensors, encoders, etc.

Example Control Systems

Figure 15:
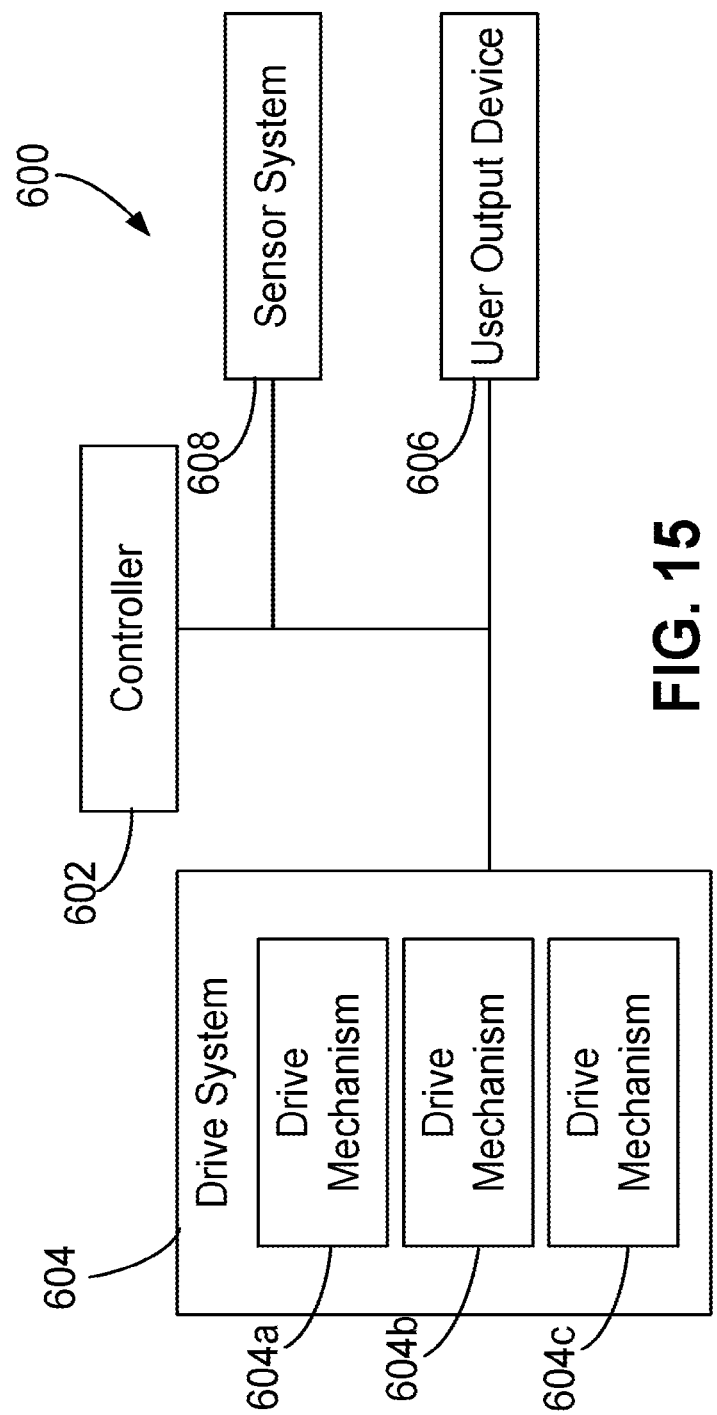
FIG. 15 is a block diagram of a control system for a system.

FIG. 15 depicts a block diagram of a control system 600 to operate the instrument 300, in particular, to generate motion of the end effector 330 of the instrument 300 in one or more DOFs, e.g., the DOF depicted in FIGS. 8-14. The control system 600 includes a controller 602 operably connected to the drive system 400 and a sensor system 608. The controller 602 is connected to the drive system 400 in a manner that enables the controller 602 to transmit control signals to drive mechanisms 604a, 604b, 604c of the drive system 400. The drive mechanism 604a includes, for example, the actuator 410. The drive mechanism 604b includes, for example, the actuator 420. The drive mechanism 604c includes, for example, the actuator 420. In this regard, the controller 602 drives the drive mechanisms 604a, 604b, 604c by generating and transmitting control signals to the actuators 410, 420, and/or 430 of the drive system 400.

The controller 602 is, for example, a controller of the drive system 400 that is operable to control electromechanical systems of the drive system 400 and the instrument 300 when the instrument 300 is coupled to the drive system 400. In some examples, the controller 602 corresponds to a controller of the manipulator system 252. The controller of the manipulator system 252 is operably connected to a controller of the drive system 400 to control operations of the drive system 400.

In some implementations, the controller 602 is operably connected to a user output device 606 to provide human-perceptible indications to a human operator, e.g., a nurse or a surgeon. The indications include, for example, one or more of a tactile, audible, or visual indication. The indications can be indicative of a force on the end effector 330, a motion of the end effector 330, or other parameter measured or sensed as described herein. The user output device 606 corresponds to, for example, a display in the operating room, a display on the operator console, a speaker, a vibrator, or other appropriate user output device. As described herein, in some implementations, the controller 602 can detect a condition associated with the instrument 300, the drive system 400, and/or the manipulator 252 based on the signals from the sensor system 608. In some implementations, the controller 602 detects an error associated with the instrument 300, the drive system 400, and/or the manipulator 252 and then issues an alert using the user output device 606 to inform the human operator of the error.

Figure 16:
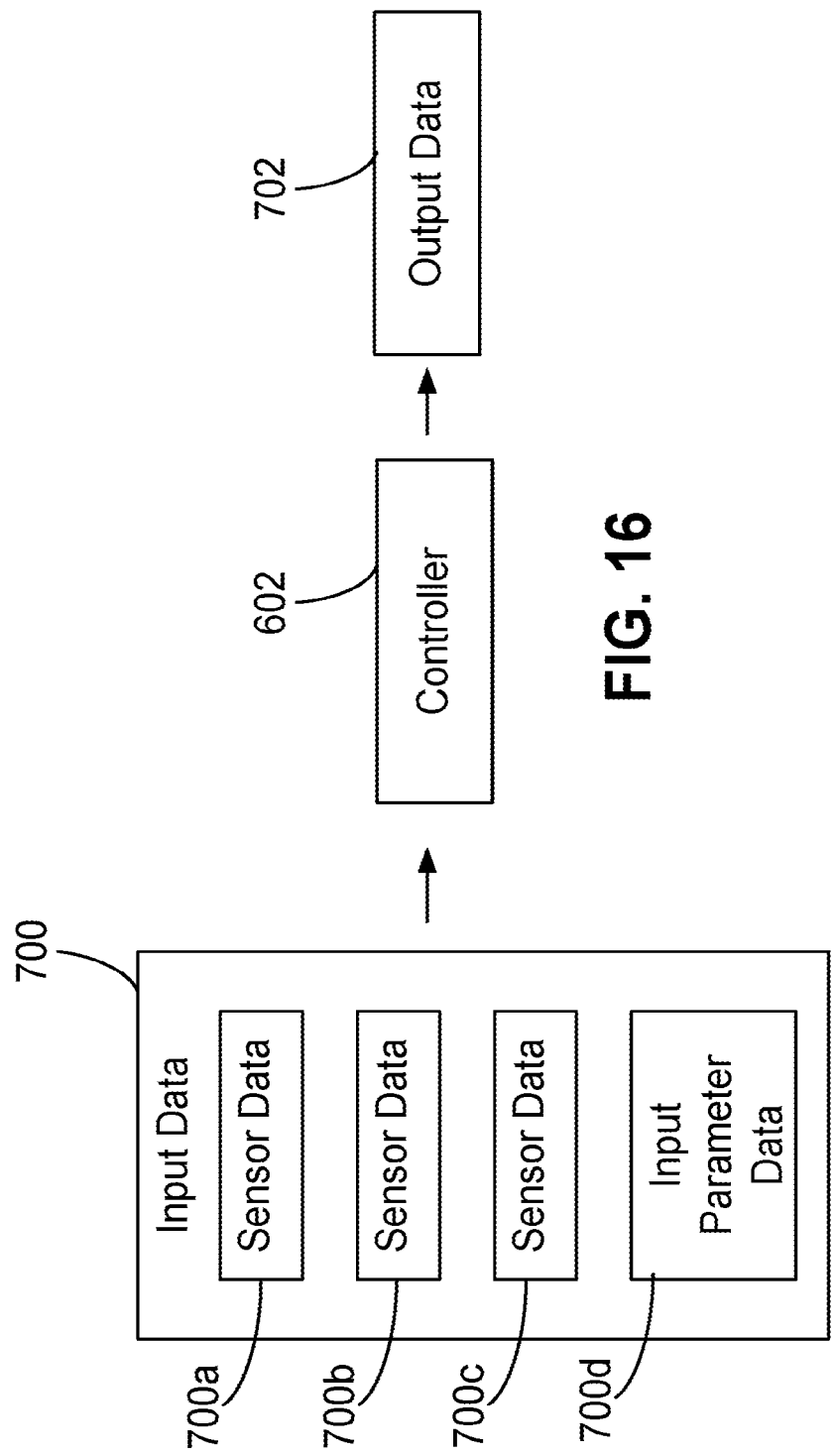
FIG. 16 is a diagram of input data and output data for a controller.

The controller 602 is connected to the sensor system 608 to receive sensor signals for generating commands based on the sensor signals. Referring to FIG. 16, the controller 602 receives input data 700 and generates output data 702 to control operations of the surgical system. The input data 700 include sensor data 700a, 700b, 700c. The sensor data 700a, 700b, 700c include data generated by the sensors of the sensor system 608. The sensor data 700a, for example, corresponds to data generated by sensors associated with the first actuator 410 and its associated drivetrain in the instrument 300. The sensor data 700b, for example, corresponds to data generated by sensors associated with the first actuator 420 and its associated drivetrain in the instrument 300. The sensor data 700c, for example, corresponds to data generated by sensors associated with the third actuator 430 and its associated drivetrain in the instrument 300.

In some examples, the input data 700 further include predefined parameter data 700d. The predefined parameter data 700d include threshold values for force, torque, position, orientation, and other values indicated by the sensor data 700a-700c. As described herein, the controller 602 can control operations based on determining that the sensor data 700a-700c is indicative of a sensor value above or below a threshold value.

The sensor signals generated by the sensor system 608 indicative of, for example, loads applied by the actuators 410, 420, 430, positions and/or orientations of the actuators 410, 420, 430, poses of the end effector 330, external loads on the end effector 330, etc. In addition to being indicative of positions and orientations of the drive mechanisms of the drive system 400 and the end effector 330 of the instrument 300, the sensor signals can be indicative of positions and/or orientations of components in the drivetrains extending between the drive mechanism and the end effector 330. Furthermore, the sensor signals can be indicative of loads on any such component. In some examples, the sensor signals are indicative of tensions, frictions, and other loads on the tensioning members 340, 360. In particular, the sensor signals can be indicative of tensions applied by the actuators 410, 420, 430.

In some implementations, the output data 702 include control signals to operate the drive mechanisms 604a-604c. The control signals are, for example, feedback control signals used to control the drive mechanisms 604a-604c to apply desired torques or to be repositioned to desired positions. In some implementations, the output data 702 include control signals to operate the user output device 606.

Example Control Processes

During a surgical operation, motion of the end effector 330 and motion of the instrument 300 are controlled through operation of the drive mechanisms 604a-604c. The motion of the end effector 330 includes, for example, motion of the end effector 330 relative to the shaft 302 and/or relative to the housing 402 of the drive system 400. The motion of the instrument 300 includes, for example, motion of the instrument 300 relative to the housing 402 of the drive system 400. The drive mechanisms 604a-604c are operated simultaneously to produce desired motions of the instrument 300 and the end effector 330 of the instrument 300. In some examples, the drive mechanisms 604a, 604b are operated to drive the tensioning members 340, 360 to reposition the end effector 330 a yaw or pitch DOF. As described with respect to a process 1700 illustrated in FIG. 17, the drive mechanism 604c is also controlled during operations of the drive mechanisms 604a, 604b so that the motion of the end effector 330 is limited to the desired yaw or pitch DOF. In some examples, the drive mechanism 604c is operated to move the instrument 300 in an insertion DOF. As described with respect to a process 1800 illustrated in FIG. 18, the drive mechanisms 604a and 604b are also operated to ensure that motion of the instrument 300 is limited to the insertion DOF.

Figure 17:
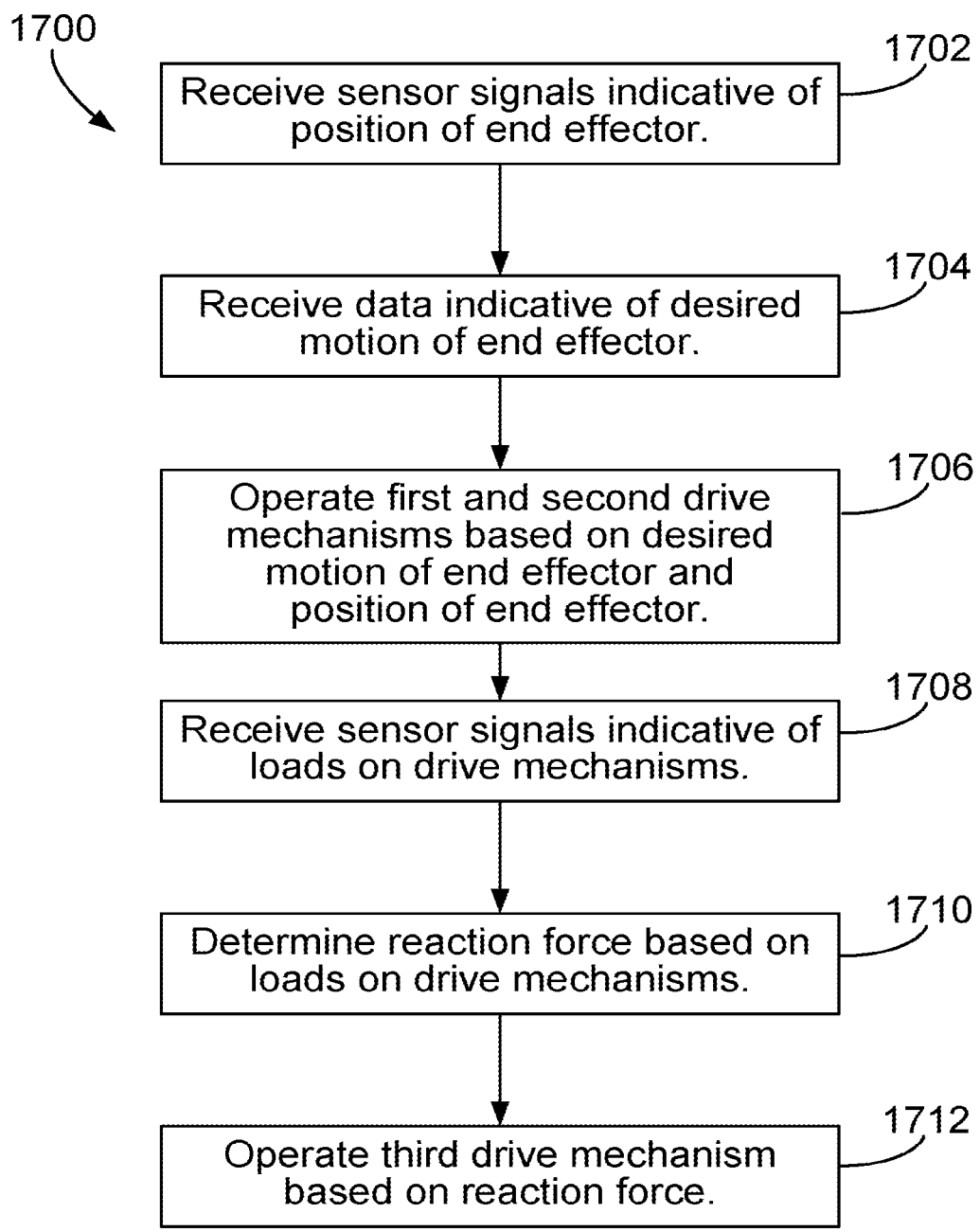
FIG. 17 is a flowchart of a process to move an end effector of an instrument.

In the process 1700 illustrated in FIG. 17, the tensioning members 340, 360 are driven based on sensor signals. At an operation 1702 of the process 1700, the controller 602 receives sensor signals indicative of a position of the end effector 330. The sensor signals are received from, for example, the sensors of the sensor system 608 described herein. In some cases, the sensor signals are also indicative of positions of the drive mechanisms 604a-604c. The signals can be indicative of positions of the actuators 410, 420, 430 of the drive mechanisms 604a-604c, the positions of the engagement members 350, 370, and/or the position of the shaft 302. In some implementations, the controller 602 also receives signals indicative of loads on the drive mechanisms 604a-604c.

At an operation 1704, the controller 602 receives data indicative of a desired motion of the end effector 330. The data corresponds to, for example, a control signal specifying a desired position of the end effector 330. The desired motion of the end effector 330 is, for example, in the pitch or yaw DOF illustrated in FIGS. 9-14. The control signal includes a command issued by the surgeon when the surgeon manipulates input devices on the operator console.

At an operation 1706, based on the desired motion of the end effector 330 and the position of the end effector, the controller 602 operates the drive mechanisms 604a, 604b. The drive mechanisms 604a and 604b are controlled, for example, to reposition the engagement members 350, 370 to desired positions relative to the shaft 302 and relative to the housing 402 of the drive system 400 so that the end effector 330 undergoes the desired motion. When the engagement members 350, 370 are repositioned, the tensioning members 340, 360 are driven to cause the desired motion of the end effector 330.

In some examples, the drive mechanisms 604 include linear actuators whose longitudinal positions are sensed by the sensor system 608. The longitudinal positions of the linear actuators are indicative of longitudinal positions of the engagement members 350, 370. Accordingly, the controller 602 controls longitudinal positions of the engagement members 350, 370 by controlling longitudinal positions of the linear actuators. The sensor signals indicative of the positions of the engagement members 350, 370 serve as feedback signals for precise control of the drive mechanisms 604a, 604b to drive the engagement members 350, 370.

At an operation 1708, the controller 602 receives sensor signals indicative of loads on the drive mechanisms 604a-604c. During the operations 1706 and 1708, the drive mechanisms 604a-604c are operated in a manner to produce different tensions in the tensioning members 340, 360. The tensions differ by an amount that drives the tensioning members 340, 360 in a manner that moves the end effector 330 to the desired position. In one example, the controller 602 can operate the actuator 410 of the drive mechanism 604a to apply a tension to the tensioning member 340 less than the tension applied by the actuator 420 of the drive mechanism 604b to the tensioning member 360. The difference in the tension generates motion of the end effector 330 in a first direction in the DOF. In another example, the controller 602 can operate the actuator 420 of the drive mechanism 604b to apply a tension to the tensioning member 360 less than the tension applied by the actuator 410 to the tensioning member 340. This difference in tension generates motion of the end effector 330 in a second direction in the DOF. In some implementations, the difference in the tension in the tensioning member 360 and the tension in the tensioning member 340

At an operation 1710, the controller 602 determines a reaction force to be applied by the drive mechanism 604c to balance the forces applied by the drive mechanisms 604a, 604b. The reaction force, when applied, can ensure that the instrument 300 does not move while the end effector motion is produced. At an operation 1712, the controller 602 operates the drive mechanisms 604a-604c based on the determined reaction force based on the reaction force. The actuator 430, for example, generates a reaction force to inhibit motion of the instrument 300 relative to the housing 402 of the drive system 400. The reaction force opposes the forces applied to the actuator engagement members 350, 370 so that the instrument 300 remains stationary relative to the housing 402 of the drive system 400 while the tensions are applied to the tensioning members 340, 360 to move the end effector 330. In some examples, the controller 602 operates the actuator 430 of the drive mechanism 604c to generate an opposing forward reaction force that balances with the net rearward directed forces applied by the drive mechanisms 604a, 604b. In this regard, the sensor signals indicative of loads on the drive mechanisms 604a, 604b, 604c serve as feedback signals for controlling the drive mechanism 604c to produce the required reaction force.

Figure 18:
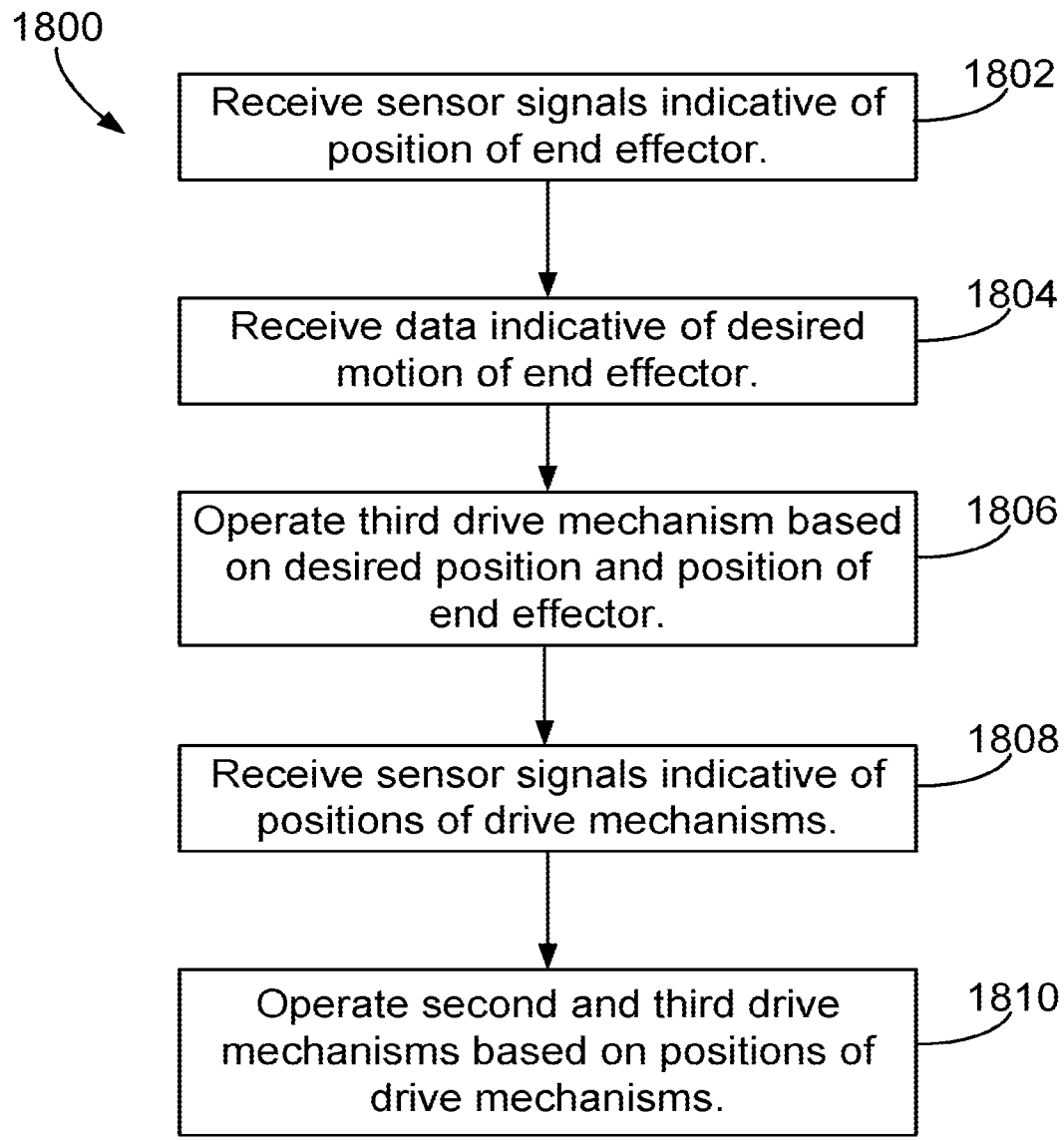
FIG. 18 is a flowchart of another process to move an end effector of an instrument.

Referring to FIG. 18, in a process 1800, the instrument 300 and the drive system 400 are operated to produce motion in the insertion DOF. At an operation 1802, the controller 602 receives sensor signals indicative of a position of the end effector 330. In particular, the sensor signals are indicative of a longitudinal position of the end effector 330 along the insertion axis of the instrument 300. The sensor signals are received from, for example, the sensors of the sensor system 608 described herein. In some cases, the sensor signals are also indicative of positions of the drive mechanisms 604a-604c. The signals can be indicative of positions of the actuators 410, 420, 430 of the drive mechanisms 604a-604c, the positions of the engagement members 350, 370, and/or the position of the shaft 302. In some implementations, the controller 602 also receives signals indicative of loads on the drive mechanisms 604a-604c.

At an operation 1804, the controller 602 receives data indicative of a desired motion of the end effector 330. The data corresponds to, for example, a control signal specifying a desired position of the end effector 330. The desired motion of the end effector 330 is, for example, in the insertion DOF illustrated in FIGS. 9-14. The control signal includes a command issued by the surgeon when the surgeon manipulates input devices on the operator console.

At an operation 1806, the controller 602 operates the drive mechanism 604c based on the desired position and the position of the end effector 330. In one example, the drive mechanism 604c is driven in a manner to move the instrument 300 a predetermined distance along the longitudinal axis. In another example, the drive mechanism 604c is operated to produce a forward force on the instrument 300. The forward force causes a motion of the instrument 300 in the distal direction, thereby enabling the instrument 300 to be inserted through the cannula 180 and into the patient.

At an operation 1808, the controller 602 receives sensor signals indicative of positions of the drive mechanisms 604a-604c. In some examples, these sensor signals are indicative of positions of the engagement members 350, 370. Alternatively, rather than or in addition to being indicative of positions of the drive mechanisms 604a, 604b, the signals are indicative of tensions on the tensioning members 340, 360.

At an operation 1810, the controller 602 operates the drive mechanisms 604a, 604b. The drive mechanisms 604a, 604b are, for example, operated to inhibit relative motion between the engagement members 350, 370 and the rest of the instrument 300. In some examples, the drive mechanisms 604a, 604b are repositioned by an amount equal to the repositioning of the drive mechanism 604c to maintain the relative positions of the engagement members 350, 370 and the shaft 302 of the instrument 300. The drive mechanism 604c is operated to cause the shaft 302 to travel a distance equal to the amount of travel of the engagement members 350, 370 enabled by the drive mechanisms 604a, 604b. In this regard, the end effector 330 does not move relative to the shaft 302 when the drive mechanism 604c is driven, and the tensions in the tensioning members 340, 360 are maintained when the drive mechanism 604c is driven. Furthermore, the engagement members 350, 370 remain stationary relative to the proximal end portion 310 as well as the shaft 302 of the instrument 300, thereby maintaining the tensions in the tensioning members 340, 360 while the instrument 300 is inserted.

In some examples, rather than being controlled based on positions of the drive mechanisms 604a-604c, the drive mechanisms 604a-604c are controlled based on sensor signals indicative of loads on the drive mechanisms 604a-604c. The drive mechanism 604c is operated to produce a forward force on the instrument 300, and the drive mechanisms 604a, 604b are operated to maintain forces on the engagement members 350, 370.

Figure 19:
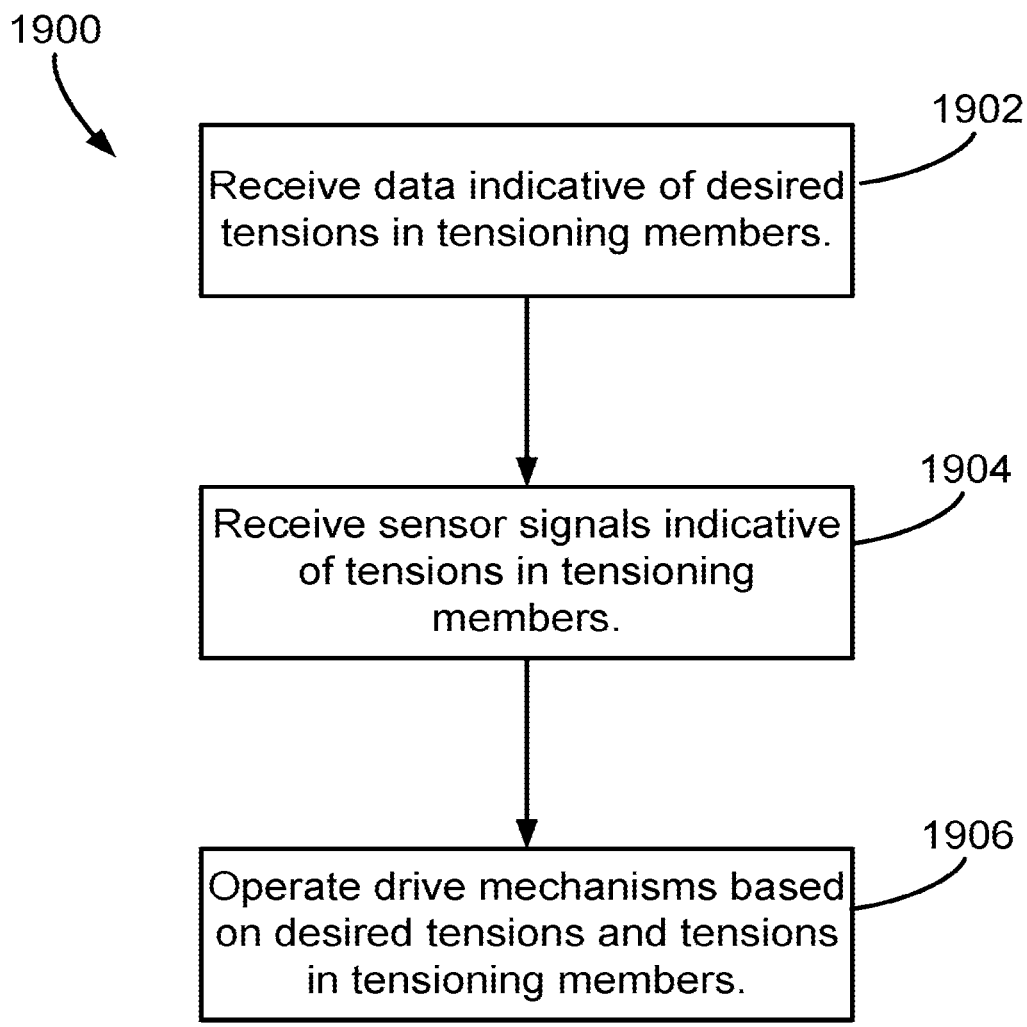
FIG. 19 is a flowchart of a process to control tensions in tensioning members of an instrument.

In some implementations, rather than being controlled to cause motion of the end effector 330, the drive mechanisms 604a-604c of the drive system 400 are controlled to detect conditions of the instrument 300 or to facilitate improved functionality of the instrument 300. In a process 1900 illustrated in FIG. 19, the controller 602 is operated in a manner to maintain tensions in the tensioning members 340, 360. At an operation 1902, the controller 602 receives data indicative of one or more applicable tension ranges for the tensioning members 340, 360. As discussed further below, in connection with operation 1906, each of the tension ranges can comprise one or more desired tensions for a tensioning member 340, 360. These one or more tension ranges are, for example, indicated by the predefined parameter data 700d.

At an operation 1904, the controller 602 receives sensor signals indicative of tensions in the tensioning members 340, 360. As described herein, these sensor signals can correspond to sensor signals indicative of loads on the drive mechanisms 604a-604c. Based on these sensed loads, the controller 602 determines the tensions on the tensioning members 340, 360.

Based on the one or more tension ranges and the tensions in the tensioning members 340, 360, at an operation 1906, the controller 602 operates the drive mechanisms 604a-604c. In some implementations, a tension range comprises a partially bounded range of tensions expressed by one or more minimum tensions, and the drive mechanisms 604a-604c are operated to cause the tensions to be above or no less than the applicable minimum tension(s). In some implementations, a tension range comprises a partially bounded range of tensions expressed by one or more maximum tensions, and the drive mechanisms 604a-604c are operated to cause the tensions to be below or no more than the applicable maximum tension(s). In some implementations, a tension range comprises one or more target tensions, and the drive mechanisms 604a-604c are operated to maintain the tensions within a defined extent of the target tensions. In some implementations, the drive mechanisms 604a-604c are operated to maintain the tensions as close to the target tensions as possible given mechanical, electrical, or other system constraints. In some implementations, the tension range comprise a bounded range of tensions expressed using one or more minimum tensions and one or more maximum tensions, and the drive mechanisms 604a-604c are operated to cause the tensions to be above or no less than the applicable minimum tension(s) and below or no more than the applicable maximum tensions(s). In some implementations, the tension range changes with the operational context, such as based on a type of the instrument, a procedure being performed, a wear condition of the flexible tensioning member or other part of the instrument, a preference of the operator, etc.

In some implementations, the tensions are considered to be in the tension ranges when the magnitudes of the tensions are greater than or no less than the magnitudes of minimum tensions. The tensions are, for example, maintained above or no less than minimum tensions in some implementations. The minimum tensions, for example, correspond to desired preloads on the tensioning members 340, 360 that can improve responsiveness of the end effector 330 to additional tensions applied to the tensioning members 340, 360. As the instrument 300 is used during the surgical operation and for subsequent surgical operations, preloads on the tensioning members 340, 360 may decrease over time, thereby reducing the responsiveness of the end effector 330 to the forced applied by the drive mechanisms 604a, 604b. To ensure that the end effector 330 remains responsive, the controller 602 can operate the drive mechanisms 604a, 604b to drive tensioning members 340, 360 to one or more desired tensions in the applicable tension range(s).

The preloads can be applied to the tensioning members 340, 360 without causing motion of the end effector 330 and/or causing motion of the instrument 300 relative to the housing 402 of the drive system 400. In this regard, the controller 602 can control the drive mechanisms 604a, 604b so that the preloads in the tensioning members 340, 360 are balanced, thereby maintaining the position of the end effector 330 at a central position. The controller 602 can also control each of the drive mechanisms 604a-604c so that the shaft 302 does not move along the longitudinal axis of the instrument 300, e.g., to prevent motion in the insertion DOF. As described with respect to the process 1700, to ensure that the instrument 300 does not move when the tensioning members 340, 360 are driven, the drive mechanism 604c is operated to produce the appropriate reaction force.

The process 1900 is used to check the preloads on the tensioning members 340, 360 and ensure that the preloads are above desired preloads. The controller 602 can implement the process 1900 when the instrument 300 is mounted onto the drive system 400 and the instrument 300 is inserted into the patient. In some implementations, the process 1900 is executed intermittently during the surgical procedure so that the preloads can be maintained above the desired preloads throughout the surgical procedure. The controller 602 performs the process 1900 using sensor data from the sensor system 608. The controller 602 determines, for example, that the preloads are below desired preloads and accordingly drives the engagement members 350, 370, and hence the tensioning members 340, 360 until the tensions in the tensioning members 340, 360 exceed the desired preloads. The load sensors associated with the drive mechanisms 604*a*, 604*b* generate the sensor data usable by the controller 602 to determine the tensions in the tensioning members 340, 360. In this regard, based on these sensor data, the controller 602 ceases driving of the engagement members 350, 370 when the tensions exceed the desired preloads.

In some implementations, the desired preloads for the tensioning members 340, 360 are the same, but the tensioning members 340, 360 experience different amounts of stretch. To achieve the desired preloads, the drive mechanisms 604*a*, 604*b* are repositioned to different positions.

In some implementations, decreased preloads on the tensioning members 340, 360 over multiple uses of the instrument 300 or over prolonged use of the instrument 300 can occur as a result of stretch of the tensioning members 340, 360. The signals from the sensor system 608 can be indicative of the amount of stretch of the tensioning members 340, 360. If the sensor system 608 includes position sensors, the position sensors can generate position signals indicative of positions of the drive mechanisms 604*a*, 604*b*, 604*c* when the drive mechanisms 604*a*, 604*b* are engaged with the engagement members 350, 370 and when the drive mechanism 604*c* is engaged with the proximal end portion 310. Based on these positions, the controller 602 can determine an amount of stretch of each of the tensioning members 340, 360. The controller 602, for example, determines the amount of stretch of the tensioning member 340 based on the position of the drive mechanism 604*a* and the position of the drive mechanism 604*c*. The controller 602, for example, determines the amount of stretch of the tensioning member 340 based on the position of the drive mechanism 604*a* and the position of the drive mechanism 604*c*. The amount of stretch in one or more of the tensioning members 340, 360 being above a predefined stretch, e.g., a threshold stretch indicated by the input parameter data 700*d*, can indicate that a lifecycle of the instrument 300 has been exhausted. The controller 602 accordingly can generate output data 702 to control the user output device 606 to issue an alert or an alarm indicative of an error associated with the instrument 300. In particular, the alert can indicate that the instrument 300 should no longer be used and that the instrument 300 should be disposed.

In some implementations, rather than corresponding to preloads, the tensions levels indicated in the received data of the operation 1902 correspond to locking tensions indicated by the input parameter data 700*d*. Tensions exceeding the locking tensions can generate sufficient friction between the tensioning members 340, 360 and another component of the instrument 300 to lock the end effector 330 and inhibit motion in the DOF controlled by the tensioning members 340, 360. The component is, for example, the pulley 332. While motion is inhibited in the DOF controlled by the tensioning members 340, 360, motion in other DOFs are allowed. For example, if the instrument 300 provides both a pitch DOF and a yaw DOF of the end effector 330, the controller 602 can operate the drive mechanisms 604*a*-604*c* to lock the end effector 330 such that motion of the end effector 330 is inhibited in the pitch DOF. The controller 602 may be operated in this manner because pitch motion may be unnecessary for the procedure, or pitch motion may cause unnecessary wear of the tensioning members 340, 360. The controller 602 can still operate other tensioning members (not shown) to control motion in the yaw DOF as well as the insertion DOF.

While the instrument 300 is described as including a shaft with an end effector at a distal portion (e.g. a distal end or other distal portion) of the shaft, in some implementations, the instrument 300 includes a flexible shaft formed from several links connected to one another. The shaft includes, for example, a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. Tensions can be applied to the tensioning members of the instrument 300 to cause motion between links. In some examples, the controller 602 operates the drive mechanisms 604*a*-604*c* to apply large tensions to the tensioning members 340, 360 to increase friction between the interconnected links of the shaft, thereby decreasing relative mobility of these links.

In some implementations, the sensor data 700*a*-700*c* generated by the sensor system 608 is usable to detect external forces on the instrument 300. External forces include, for example, friction on the shaft 302 of the instrument 300. As the shaft 302 of the instrument 300 is inserted through the cannula 180, contact between the shaft 302 and the cannula 180 may result in friction forces on the shaft 302. The friction forces may be detectable by the sensors of the sensor system 608. For example, while the drive mechanism 604*c* is operated to cause the shaft 302 to travel a predetermined distance, sensors of the sensor system 608 can generate signals indicative of higher forces while the shaft 302 is inserted through the cannula 180. The controller 602 can operate the drive mechanisms 604*a*-604*c* to compensate for the friction forces on the shaft 302. In particular, the drive mechanism 604*c* can be operated to apply higher loads to overcome the friction force and to thereby reposition the shaft 302. The drive mechanisms 604*a*, 604*b*, if necessary, can be operated to maintain the positions of the engagement members 350, 370 relative to the proximal end portion 310 in accordance to the processes described herein.

In some examples, if the force is higher than a predefined force indicated in the input parameter data 700*d*, the controller 602 determines that an error in operation has occurred. In particular, the controller 602 determines that the friction force is too high. In some implementations, the excessive friction force is indicative of a misalignment between drive system 400 and the instrument 300, a misalignment between the cannula 180 and the instrument 300, and/or a misalignment between the cannula 180 and the drive system 400. When the friction force is too high, the controller 602 can operate the user output device 606 to generate an alert or alarm to indicate an error in the insertion operation. The human operator can perform a corrective action to correct the source of the error, e.g., by correcting alignment of the component of the surgical system.

In some implementations, the controller 602 can detect a breakage or a malfunction of instrument 300 or the drive system 400. For example, in some implementations, the controller 602 can determine a break in one or more of the tensioning members 340, 360 based on the sensors of the sensor system 608. The sensors, for example, can generate sensor signals indicative of a sudden decrease in force, if such a sudden decrease in force occurs. The sensors can include any type of sensors that can generate signals indicative of changes in force, such as force sensors, position sensors, accelerometers, or other appropriate sensors. These sensor signals are, for example, indicative of a sudden decrease in tension in one or more of the tensioning members 340, 360. In some examples, if the tensioning member 340 breaks, the force signal generated by the sensor associated with the drive mechanism 604a indicates a sudden drop in force. If the tensioning member 360 breaks, the force signal generated by the sensor associated with the drive mechanism 604b indicates a sudden drop in force. If the tensioning member 340 and the tensioning member 360 form a continuous cable, both the force sensor associated with the drive mechanism 604a and the sensor associated with the drive mechanism 604b generate signals indicative of sudden drops in force. If the tensioning members 340, 360 are coupled to another component at a distal portion (e.g. a distal end or some other distal portion) of the instrument 300, the sensors may both still generate signals indicative of sudden drops in force, but the sudden drop may be greater in magnitude for the sensor associated with the broken tensioning member. In some examples, the sensor associated with the drive mechanism 604c also generates a signal indicative of the break. Because the drive mechanism 604c generates the reaction force to the tensions in the tensioning members 340, 360, a sudden drop in tension in any of the tensioning members 340, 360 can result in a sudden drop in a force on the drive mechanism 604c. Based on these force signals from any of these sensors, the controller 602 can detect a break in one or more tensioning members 340, 360. Furthermore, in some examples, the controller 602 detects which of the tensioning members 340, 360 has experienced the break, e.g., based on a difference in tensions in the tensioning members 340, 360 indicated by the sensor signals.

In some implementations, the sensor signals are indicative of forces on the end effector 330. As the end effector 330 contacts the anatomy of the patient, the patient tissue can exert forces on the end effector 330. The forces on the end effector 330 are detectable by the force sensors associated with the drive mechanisms 604a-604c. For example, if the end effector 330 contacts an object, e.g., patient tissue, while performing the motion facilitated by the tensioning members 340, 360, the force sensors generate signals indicative of the contact. In some implementations, the force signals may be used to control motion of the end effector 330 and hence be used to control manipulation of the tissue by the end effector 330. For example, the amount of power that the drive mechanisms 604a-604c transferred to the tissue can be controlled based on the force signals. In some cases, the forces indicated by the force signals can be maintained within a predefined range for controlling the manipulation of the tissue by the end effector 330. In some implementations, the controller 602 can generate human-perceptible indications indicative of forces on the end effector 330. For example, the controller 602 can provide haptic feedback indicative of the force on the end effector 330 detected by the sensor system 608. In some implementations, the force signals may indicate a sudden increase in force indicative of contact with the object. The controller 602 can prevent further actuation of the drive mechanisms 604a-604c in this manner to inhibit a high application of force to the object. In some examples, the controller 602 provides an alert or alarm when the sensor signals is indicative of a force exerted by the end effector that exceeds a threshold force. In some examples, the controller 602 only allows movement away from the object, thereby inhibiting the end effector 330 from being driven further into the object. In some implementations, the controller 602 issues an alert indicative of the contact or indicative of a force detected by the force sensors exceeding a predefined force, e.g., indicated by the input parameter data 700d.

Example Computer Systems

Figure 20:
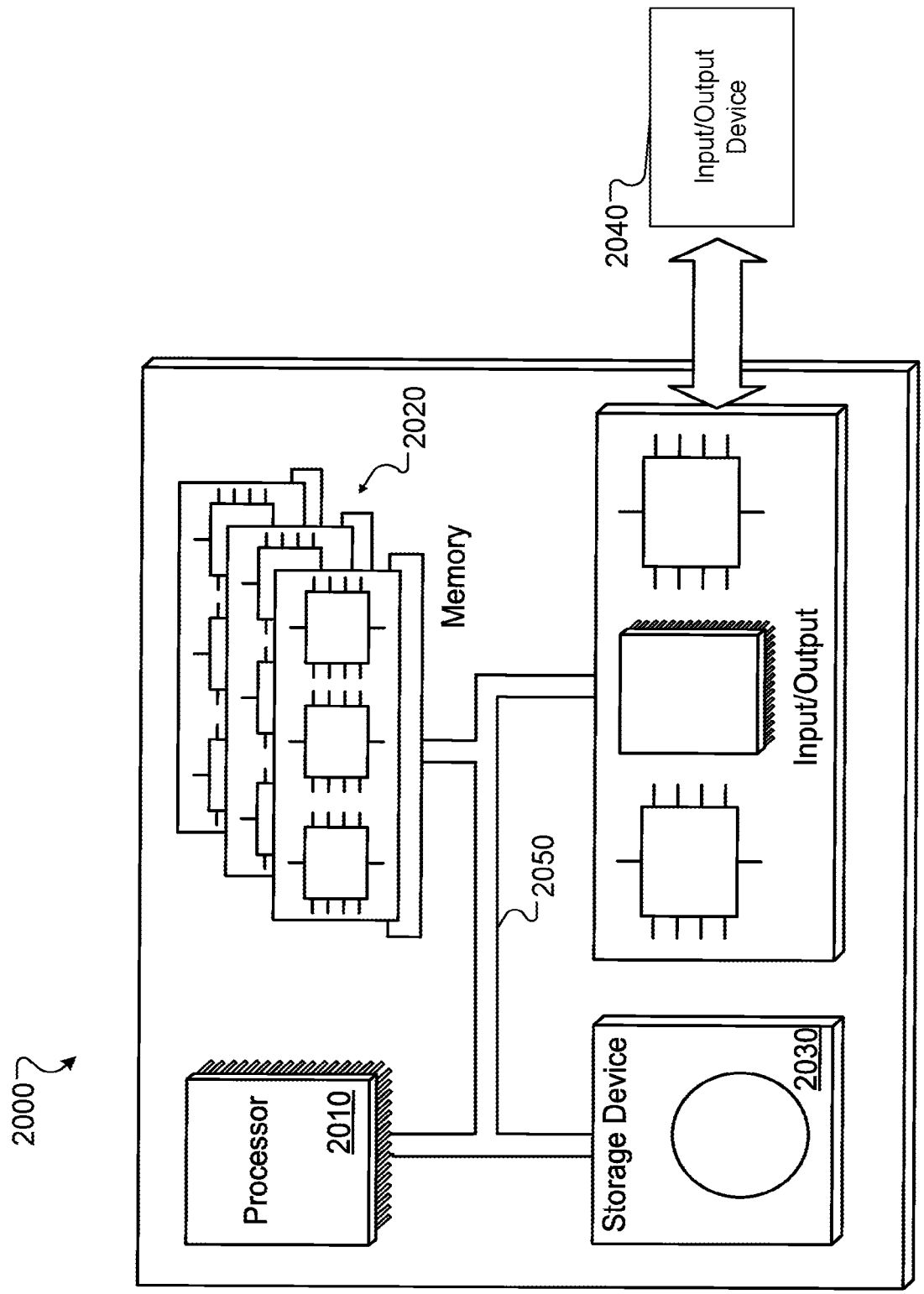
FIG. 20 is a schematic diagram of a computer system.

Controllers and any associated components described herein can be part of a computing system that facilitates control of the insertion systems according to processes and methods described herein. FIG. 20 is a schematic diagram of an example of a computer system 2000 that can be used to implement a controller, e.g., the controller of the drive system 400, a controller of the manipulator system 252, a controller of the patient-side cart 100, etc., described in association with any of the computer-implemented methods described herein. The system 2000 includes components such as a processor 2010, a memory 2020, a storage device 2030, and an input/output device 2040. Each of the components 2010, 2020, 2030, and 2040 are interconnected using a system bus 2050. The processor 2010 is capable of processing instructions for execution within the system 2000. In some examples, the processor 2010 is a single-threaded processor, while in some cases, the processor 2010 is a multi-threaded processor. The processor 2010 is capable of processing instructions stored in the memory 2020 or on the storage device 2030 to display graphical information for a user interface on the input/output device 2040.

Memory storage for the system 2000 can include the memory 2020 as well as the storage device 2030. The memory 2020 stores information within the system 2000. The information can be used by the processor 2010 in performing processes and methods described herein. In some examples, the memory 2020 is a computer-readable storage medium. The memory 2020 can include volatile memory and/or non-volatile memory. The storage device 2030 is capable of providing mass storage for the system 2000. In general, the storage device 2030 can include any non-transitory tangible media configured to store computer readable instructions. Optionally, the storage device 2030 is a computer-readable medium. Alternatively, the storage device 2030 may be a floppy disk device, a hard disk device, an optical disk device, or a tape device.

The system 2000 includes the input/output device 2040. The input/output device 2040 provides input/output operations for the system 2000. In some examples, the input/output device 2040 includes a keyboard and/or pointing device. In some cases, the input/output device 2040 includes a display unit for displaying graphical user interfaces.

The features of the methods and systems described in this application can be implemented in digital electronic circuitry, or in computer hardware, firmware, or in combinations of them. The features can be implemented in a computer program product tangibly stored in an information carrier. The information carrier can be, for example, a machine-readable storage device, for execution by a programmable processor. Operations can be performed by a programmable processor executing a program of instructions to perform the functions described herein by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages. The computer program can be deployed in any form, including as a stand-alone program or as a module, component, subroutine, or other unit suitable for use in a computing environment.

Generally, a computer will also include, or be operatively coupled to communicate with, one or more mass storage devices for storing data files. Such devices can include magnetic disks, such as internal hard disks and removable disks, magneto-optical disks, and optical disks. Storage devices suitable for storing the computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Alternatively, the computer can have no keyboard, mouse, or monitor attached and can be controlled remotely by another computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network. The relationship of client and server arises by virtue of computer programs running on the respective computers and having a client-server relationship to each other.

The processor 2010 carries out instructions related to a computer program. The processor 2010 can include hardware such as logic gates, adders, multipliers and counters. The processor 2010 can further include a separate arithmetic logic unit (ALU) that performs arithmetic and logical operations.

Alternative Implementations

While both the actuators 410, 420 are illustrated and described with respect to FIGS. 9-14, in some implementations, one of the drive mechanisms 604a, 604b includes an actively driven actuator while the other of the drive mechanisms 604a, 604b includes a passive component that responds to the loads applied by the actuator. In some examples, the drive mechanism 604a includes an actuator, and the drive mechanism 604b includes a resilient member, e.g., a spring. The actuator of the drive mechanism 604a is operated to drive the tensioning member 340 and the tensioning member 360, and the resilient member of the drive mechanism 604b expands in response to the driving load applied by the actuator of the drive mechanism 604a. When the actuator is operated to release the load applied to the tensioning member 340 and the tensioning member 360, the resilient member is biased towards its neutral position, thereby driving the tensioning members 340, 360. In this regard, only one actuator is actively operated to generate tensions in the tensioning members 340, 360.

While the tensioning members 340, 360 are described as flexible cables in some implementations, in other implementations, the tensioning members 340, 360 are rods. The actuators 410, 420 can be driven to push and/or pull the rods, thereby causing motion of the end effector 330. The rods are coupled to one another, for example, through a pivot coupled to the end effector 330.

Specific words chosen to describe one or more implementations herein are not intended to limit the scope of this disclosure. For example, spatially relative terms—such as "beneath", "below", "lower", "above", "upper", "proximal", "distal", and the like—when used spatially may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device positions and orientations. The combination of a body's position and orientation define the body's pose.

It should be understood that the diminutive scale of the disclosed structures and mechanisms creates unique mechanical conditions and difficulties with the construction of these structures and mechanisms that are unlike those found in similar structures and mechanisms constructed at a larger scale, because forces and strengths of materials do not scale at the same rate as the size of the mechanisms. For example, an instrument having an 8 mm shaft diameter cannot simply be scaled down to a 5 mm shaft diameter due to mechanical, material property, and manufacturing considerations. Likewise, a 5 mm shaft diameter device cannot simply be scaled down to a 3 mm shaft diameter device. Significant mechanical concerns exist as physical dimensions are reduced.

Particular implementations have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An instrument system comprising:
   a instrument comprising:
      a first engagement member disposed at a proximal portion of the instrument,
      a second engagement member disposed at the proximal portion,
      a third engagement member disposed at the proximal portion,
      an end effector disposed at a distal portion of the instrument, and
      a flexible tensioning member extending between the distal portion and the proximal portion;
   a drive system comprising:
      a first drive mechanism configured to engage with the first engagement member,
      a second drive mechanism configured to engage with the second engagement member,
      a third drive mechanism configured to engage with the third engagement member;
   a sensor configured to generate a signal indicative of a force applied by the drive system or by the end effector; and
   a controller operably coupled to the first drive mechanism, the second drive mechanism, the third drive mechanism, and the sensor, wherein the controller is configured to:
      operate the first, second, and third drive mechanisms to apply a desired tension to the flexible tensioning member, the signal being generated by the sensor while the first, second, and third drive mechanisms are operated to apply the desired tension, and
      determine whether a malfunction associated with the flexible tensioning member exists based on at least the signal.

2. The instrument system of claim 1, wherein the controller is configured to determine whether the malfunction associated with the flexible tensioning member exists based on at least the signal by:
   determining that the signal is indicative of a breakage of the flexible tensioning member.

3. The instrument system of claim 1, wherein the controller is configured to determine whether the malfunction associated with the flexible tensioning member exists based on at least the signal by:
   determining that the signal is indicative of a sudden change in the force applied by the drive system or by the end effector.

4. The instrument system of claim 3, wherein the sudden change is a sudden decrease.

5. The instrument system of claim 1, wherein the controller is configured to determine whether the malfunction associated with the flexible tensioning member exists based on at least the signal by:
   determining whether the signal indicates that the force exceeds a threshold.

6. The instrument system of claim 1, wherein:
   the force corresponds to a tension existing in the flexible tensioning member; and
   the controller is configured to determine whether the malfunction associated with the flexible tensioning member exists based on at least the signal by:
      determining that the signal is indicative of a decrease in the tension existing in the flexible tensioning member.

7. The instrument system of claim 1, wherein:
   the sensor is a first sensor, the signal is a first signal, and the force is a first force applied by the drive system;
   the instrument system further comprises: a second sensor configured to generate a second signal indicative of a second force applied by the drive system while the first, second, and third drive mechanisms are operated to apply the desired tension; and
   the controller is configured to determine whether the malfunction associated with the flexible tensioning member exists based on at least the first signal by: using at least the first signal and the second signal.

8. The instrument system of claim 7, wherein using at least the first signal and the second signal comprises:
   determining a difference in the first signal and the second signal.

9. The instrument system of claim 7, wherein:
   the flexible tensioning member comprises a first portion extending between the distal portion and the first engagement member, and a second portion extending between the end effector and the second engagement member; and
   the first force is a first tension applied by the drive system to the first portion, and the second force is a second tension applied by the drive system to the second portion.

10. The instrument system of claim 7, wherein:
    the first drive mechanism is configured to apply the first force; and
    the second drive mechanism is configured to apply the second force.

11. The instrument system of claim 1, wherein:
    the instrument further comprises: an elongate shaft extending from the proximal portion of the instrument to the distal portion of the instrument;
    the end effector is disposed on a distal portion of the elongate shaft; and
    the third engagement member is coupled to the shaft and configured to transmit forces from the third drive mechanism to the shaft.

12. The instrument system of claim 11, wherein:
    the flexible tensioning member is coupled to the first engagement member, or the second engagement member, or both the first engagement member and the second engagement member.

13. The instrument system of claim 1, further comprising:
    a user output device; wherein
    the controller is further configured to provide an alert using the user output device in response to determining that the malfunction associated with the flexible tensioning member exists.

14. An instrument drive system comprising:
    a first drive actuator configured to engage with a first engagement member of an instrument,
    a second drive actuator configured to engage with a second engagement member of the instrument,
    a third drive actuator configured to engage with a third engagement member of the instrument;
    a sensor configured to generate a signal indicative of a force applied by the instrument drive system or an end effector of the instrument; and
    a controller operably coupled to the first drive actuator, the second drive actuator, the third drive actuator, and the sensor, wherein the controller is configured to:

operate the first, second, and third drive actuators to apply a desired tension to a flexible tensioning member of the instrument, the signal being generated while the first, second, and third drive actuators are operated to apply the desired tension, and determine whether a malfunction associated with the flexible tensioning member exists based on at least the signal.

15. The instrument drive system of claim 14, wherein the controller is configured to determine whether the malfunction associated with the flexible tensioning member exists based on at least the signal by:

determining that the signal is indicative of a sudden change in the force applied by the instrument drive system or by the end effector.

16. The instrument drive system of claim 14, wherein:

the force corresponds to a tension existing in the flexible tensioning member; and the controller is configured to determine whether the malfunction associated with the flexible tensioning member exists based on at least the signal by:

determining that the signal is indicative of a decrease in the tension existing in the flexible tensioning member.

17. The instrument drive system of claim 14, wherein:

the sensor is a first sensor, the signal is a first signal, and the force is a first force applied by the instrument drive system;

the instrument drive system further comprises:

a second sensor configured to generate a second signal indicative of a second force applied by the instrument drive system while the first, second, and third drive actuators are operated to apply the desired tension; and the controller is configured to determine whether the malfunction associated with the flexible tensioning member exists based on at least the first signal by:

determining a difference in the first signal and the second signal.

18. The instrument drive system of claim 14, wherein:

the flexible tensioning member of the instrument is coupled to the first engagement member, the second engagement member, or both the first and second engagement members; and the third engagement member is coupled to an elongate shaft of the instrument.

19. A method comprising:

operating first, second, and third drive actuators of a drive system to apply a desired tension to a flexible tensioning member of a instrument, the first, second, and third drive actuators engaged with first, second, and third engagement members of the instrument disposed at a proximal portion of the instrument;

while the first, second, and third drive actuators are operated to apply the desired tension, receiving a signal indicative of a force applied by an end effector of the instrument or the drive system; and determining whether a malfunction associated with the flexible tensioning member exists based on at least the signal.

20. The method of claim 19, wherein determining whether the malfunction associated with the flexible tensioning member exists based on at least the signal comprises:

determining that the signal is indicative of a sudden change in the force applied by the drive system or by the end effector; or determining whether the signal indicates that the force exceeds a threshold; or determining that the signal is indicative of a decrease in the tension existing in the flexible tensioning member.

21. The method of claim 19, wherein:

the signal is a first signal, and the force is a first force applied by the drive system;

the method further comprises:

while the first, second, and third drive actuators are operated to apply the desired tension, receiving a second signal indicative of a second force applied by the drive system; and determining whether the malfunction associated with the flexible tensioning member exists based on at least the first signal comprises:

determining a difference between the first signal and the second signal.

* * * * *